United States Patent
Lewis et al.

(10) Patent No.: US 11,041,134 B2
(45) Date of Patent: *Jun. 22, 2021

(54) ALKYLATED ANISOLE-CONTAINING LUBRICATING OIL BASE STOCKS AND PROCESSES FOR PREPARING THE SAME

(71) Applicant: ExxonMobil Chemical Patents Inc., Baytown, TX (US)

(72) Inventors: Kyle G. Lewis, Houston, TX (US); Beth A. Fitch, Houston, TX (US); Wenning W. Han, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/945,322

(22) Filed: Jul. 31, 2020

(65) Prior Publication Data

US 2020/0362258 A1 Nov. 19, 2020

Related U.S. Application Data

(62) Division of application No. 15/830,484, filed on Dec. 4, 2017, now Pat. No. 10,774,282.

(Continued)

(51) Int. Cl.
*C10M 105/18* (2006.01)
*C07C 41/30* (2006.01)
(Continued)

(52) U.S. Cl.
CPC ........... *C10M 105/18* (2013.01); *C07C 41/30* (2013.01); *C07C 43/205* (2013.01);
(Continued)

(58) Field of Classification Search
CPC ............ C10N 2240/04; C10N 2240/10; C10N 2020/02; C10N 2020/085; C10N 2030/06;
(Continued)

(56) References Cited

U.S. PATENT DOCUMENTS

| 5,202,040 A | * | 4/1993 | Sanderson | ........... C10M 111/04 508/580 |
| 6,548,709 B2 | * | 4/2003 | Wu | ........................ C07C 319/14 568/38 |

FOREIGN PATENT DOCUMENTS

| JP | H7(1995)-258116 A | 10/1995 |
| JP | H11(1999)-181456 | 7/1999 |

* cited by examiner

*Primary Examiner* — Vishal V Vasisth

(57) ABSTRACT

Compounds having the formula (F-I) below are provided herein:

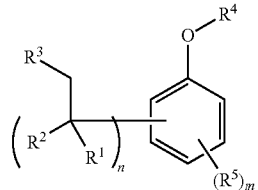

(F-I)

wherein $R^1$ and $R^2$ at each occurrence are independently a $C_1$-$C_{5000}$ alkyl group; $R^3$ at each occurrence is independently hydrogen or a $C_1$-$C_{5000}$ alkyl group; $R^4$ is a $C_1$-$C_{50}$ alkyl group or an unsubstituted or substituted phenyl group; $R^5$ at each occurrence is independently hydrogen or a $C_1$-$C_{30}$ alkyl group; n is 1, 2, 3, or 4; and m+n is 5. Processes for preparing compounds of formula (F-I) as well as base stock and lubricant compositions containing compounds of formula (F-I) are also provided.

11 Claims, 9 Drawing Sheets

Related U.S. Application Data

(60) Provisional application No. 62/446,933, filed on Jan. 17, 2017, provisional application No. 62/439,653, filed on Dec. 28, 2016, provisional application No. 62/439,660, filed on Dec. 28, 2016.

(51) Int. Cl.
*C07C 43/205* (2006.01)
*C10N 40/04* (2006.01)
*C10N 40/25* (2006.01)

(52) U.S. Cl.
CPC . *C10M 2207/0406* (2013.01); *C10N 2040/04* (2013.01); *C10N 2040/25* (2013.01)

(58) Field of Classification Search
CPC ............ C10N 2030/08; C10N 2030/10; C10N 2030/74; C10N 2040/04; C10N 2040/25; C10N 2070/00; C07C 43/205; C07C 41/30; C10M 105/18; C10M 2207/0406; C10M 2207/04
See application file for complete search history.

ALKYLATED ANISOLE-CONTAINING LUBRICATING OIL BASE STOCKS AND PROCESSES FOR PREPARING THE SAME

PRIORITY CLAIMS

This application is a divisional application of U.S. application Serial No. 15/830,484 filed Dec. 4, 2017, now U.S. Pat. No. 10,774,282, which claims the benefit of United States Provisional Application No. 62/446,933, filed Jan. 17, 2017; U.S. Provisional Application No. 62/439,653, filed Dec. 28, 2016 (2016EM350); and U.S. Provisional Application No. 62/439,660, filed Dec. 28, 2016 (2016EM351), the disclosures of which are incorporated by reference herein in their entirety.

FIELD OF THE INVENTION

This disclosure relates to alkylated anisole compounds, processes for producing the alkylated anisole compounds, and lubricating oil base stocks and lubricating oils including the alkylated anisole compounds.

BACKGROUND OF THE INVENTION

Lubricants in commercial use today are prepared from a variety of natural and synthetic base stocks admixed with various additive packages and solvents depending upon their intended application. Trends in automotive and industrial lubrication require formulations to achieve improved energy and fuel efficiency as well as greater stability. To achieve improved energy efficiency may require use of base stocks with lower viscosity, improved friction and lower traction. Although, at the same time, base stocks must also remain durable in increasingly severe conditions including high temperature and high workloads. Further, it is desirable that base stocks resist chemical degradation from common environmental elements, such as oxygen and water.

One category of base stocks, Group V base stocks, which are synthetic base stocks, find application in automotive and industrial lubricant formulations. Examples of Group V base stocks include esters, alkylated aromatics (e.g., alkylated naphthalenes), and polyalkylene glycols (PAGs). Group V base stocks are often incorporated into lubricant formulations to improve the solubility of additives, improve deposit performance, reduce volatility, and/or enhance the thermal-oxidative stability of the lubricant. However, it is difficult for a base stock to have a combination of such desirable properties. For example, esters are polar base stocks that help solubilize additives in hydrocarbon base stocks. However, esters may be susceptible to hydrolytic break down. Further, due to their high polarity, esters may interfere with an anti-wear additive's ability to interact with metal surfaces, thereby limiting esters' efficacies. Additionally, the polarity of esters can also cause incompatibilities with elastomer seals.

As another example, alkylated aromatics, particularly alkylated naphthalenes, have high oxidative stability. However, since alkylated naphthalenes are less polar than esters, they are not as capable as esters in solubilizing additives in the hydrocarbon base stocks. Furthermore, alkylated naphthalenes may have high pour points resulting in poor low temperature fluidity.

Therefore, there is a need for synthetic base stocks that can achieve a combination of desirable properties, including but not limited to: 1) improved low temperature fluidity, 2) low volatility, 3) high thermal-oxidative stability, and 4) low viscosity.

SUMMARY OF THE INVENTION

It has been found that alkylated anisoles having enhanced low temperature fluidity, low volatility, high thermal and oxidative stability as well as low viscosity can be achieved by contacting an anisole-derivative compound with an unhydrogenated polyalpha-olefin (uPAO) in the presence of an acid catalyst.

Thus, this disclosure relates in part to a compound having the formula (F-I) below:

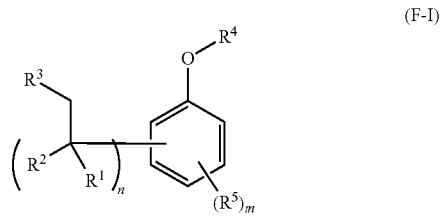

wherein $R^1$ and $R^2$ at each occurrence are independently a $C_1$-$C_{5000}$ alkyl group; $R^3$ at each occurrence is independently hydrogen or a $C_1$-$C_{5000}$ alkyl group; $R^4$ is a $C_1$-$C_{50}$ alkyl group or an unsubstituted or substituted phenyl group; $R^5$ at each occurrence is independently hydrogen or a $C_1$-$C_{30}$ alkyl group; n is 1, 2, 3, or 4; and m+n is 5.

This disclosure also relates in part to a process for making a compound of formula (F-I), the process comprising reacting a compound having the following formula (F-Ia):

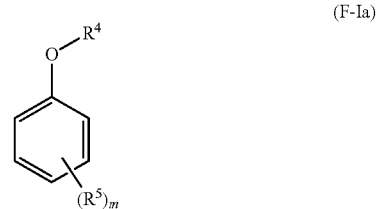

with an olefin-containing material comprising a compound having the following formula (F-Ib):

in the presence of an acid catalyst.

This disclosure yet further relates in part to a lubricant base stock comprising one or more of the compounds of formula (F-I).

This disclosure further relates in part to a formulated lubricant comprising one or more of the lubricant base stocks described herein.

Other embodiments, including particular aspects of the embodiments summarized above, will be evident from the detailed description that follows.

DETAILED DESCRIPTION OF THE INVENTION

Figure 1:
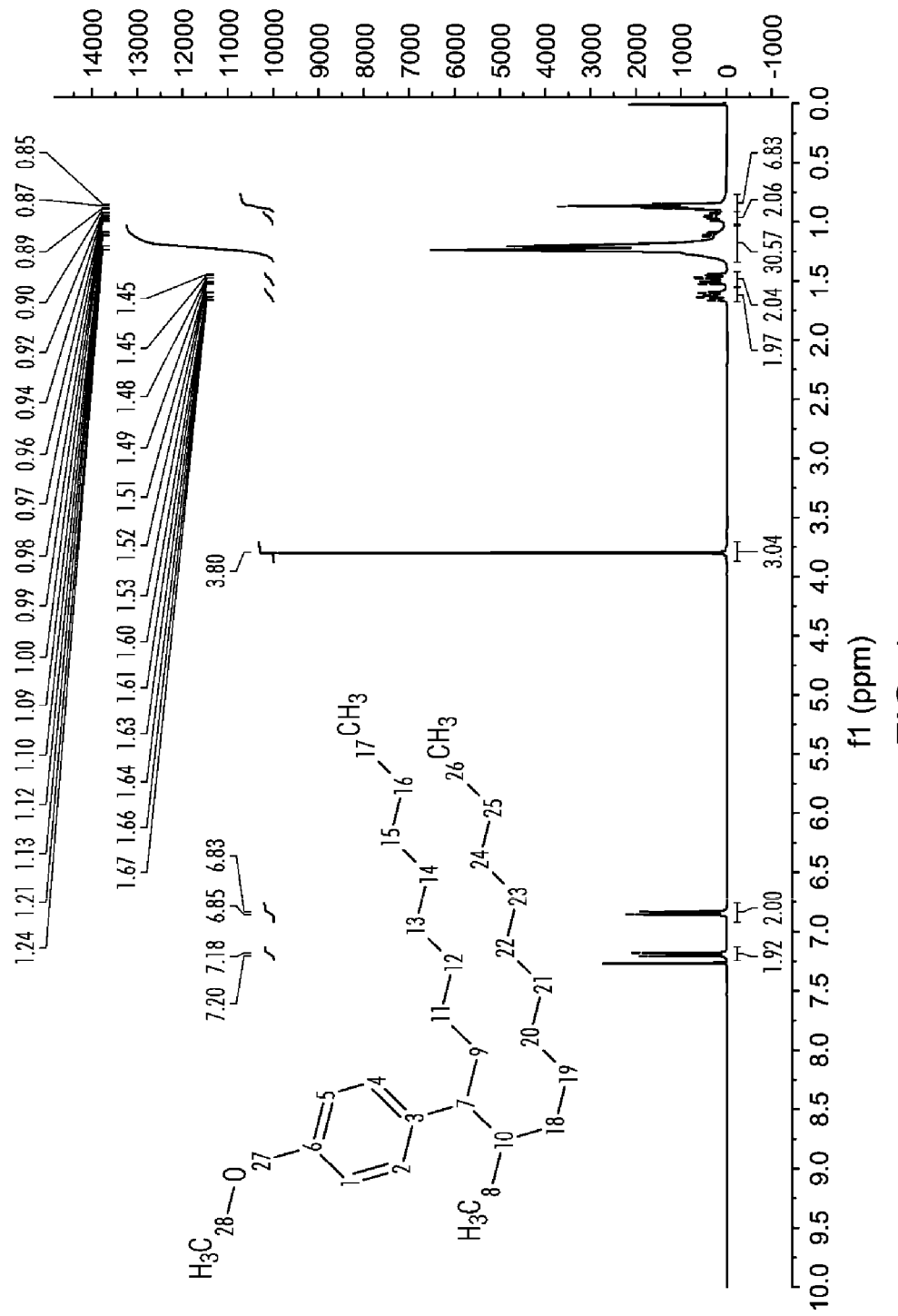
FIG. 1 illustrates $^1$H NMR spectra of Product I in the Examples of this disclosure.

In various aspects of the invention alkylated anisole compounds of formula F-I, processes for producing the alkylated anisole compounds, and lubricating oil base stocks and lubricating oils including the alkylated anisole compounds are provided herein.

I. Definitions

For purposes of this invention and the claims hereto, the numbering scheme for the Periodic Table Groups is according to the IUPAC Periodic Table of Elements as of Jan. 1, 2017.

The term "and/or" as used in a phrase such as "A and/or B" herein is intended to include "A and B", "A or B", "A", and "B".

The terms "substituent", "radical", "group", and "moiety" may be used interchangeably.

As used herein, and unless otherwise specified, the term "C" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

As used herein, and unless otherwise specified, the term "alkyl" refers to a saturated hydrocarbon radical having from 1 to 1000 carbon atoms (i.e. $C_1$-$C_{1000}$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl (—$CH_3$), "$C_2$ alkyl" refers to ethyl (—$CH_2CH_3$), "$C_3$ alkyl" refers to propyl (—$CH_2CH_2CH_3$) and isopropyl, and "$C_4$ alkyl" refers to the butyl groups (e.g. —$CH_2CH_2CH_2CH_3$, —$CH(CH_3)CH_2CH_3$, —$CH_2CH(CH_3)_2$, etc.). Further, as used herein, "Me" refers to methyl, "Et" refers to ethyl, "i-Pr" refers to isopropyl, "t-Bu" refers to tert-butyl, and "Np" refers to neopentyl.

As used herein, and unless otherwise specified, the term "aromatic" refers to unsaturated hydrocarbons comprising an aromatic ring in structures thereof, the aromatic ring having a delocalized conjugated π system and preferably having from 4 to 20 carbon atoms. Exemplary aromatics include, but are not limited to, benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. The aromatic may optionally be substituted, e.g., with one or more alkyl group, alkoxy group, halogen, etc. The aromatic ring may comprise one or more heteroatoms. Examples of heteroatoms include, but are not limited to, nitrogen, oxygen, and/or sulfur. Aromatics with one or more heteroatom in the aromatic ring therein include, but are not limited to, furan, benzofuran, thiophene, benzothiophene, oxazole, thiazole and the like, and combinations thereof. The aromatic ring may be monocyclic, bicyclic, tricyclic, and/or polycyclic (in some embodiments, at least monocyclic rings, only monocyclic and bicyclic rings, or only monocyclic rings) and may take the form of fused rings.

As used herein, the term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be straight-chain, branched-chain or cyclic. "Olefin" is intended to embrace all structural isomeric forms of olefins, unless it is specified to mean a single isomer or the context clearly indicates otherwise.

As used herein, the term "alpha-olefin" refer to an olefin having a terminal carbon-to-carbon double bond (($R^1R^2$)—C=$CH_2$) in the structure thereof.

As used herein, "polyalpha-olefin(s)" ("PAO(s)") includes any oligomer(s) and polymer(s) of one or more alpha-olefin monomer(s). Thus, the PAO can be a dimer, a trimer, a tetramer, or any other oligomer or polymer comprising two or more structure units derived from one or more alpha-olefin monomer(s). The PAO molecule can be highly regio-regular, such that the bulk material exhibits an isotacticity, or a syndiotacticity when measured by $^{13}$C NMR. The PAO molecule can be highly regio-irregular, such that the bulk material is substantially atactic when measured by $^{13}$C NMR. A PAO material made by using a metallocene-based catalyst system is typically called a metallocene-PAO ("mPAO"), and a PAO material made by using traditional non-metallocene-based catalysts (e.g., Lewis acids, supported chromium oxide, and the like) is typically called a conventional PAO ("cPAO").

A PAO molecule as obtained from the polymerization or oligomerization of alpha-olefin monomers, without further hydrogenation thereof, typically contains an ethylenically unsaturated C=C double bond in the structure thereof. An unhydrogenated PAO is sometimes referred to as a "uPAO" herein. A uPAO material could comprise, among others, vinyls (F-A below, where R is an alkyl), 2,2-di-substituted olefins (F-B below, also-known-as vinylidenes, where $R^1$ and $R^2$, the same or different, are alkyl groups), 1,2-di-substituted olefins (including the E- and Z-isomers of F-C1 and F-C2 below, also-known-as di-substituted vinylenes, where $R^1$ and $R^2$, the same or different, are alkyl groups), and tri-substituted olefins (F-D below, also-known-as tri-substituted vinylenes, where $R^1$, $R^2$, and $R^3$, the same or different, are alkyl groups). The vinyls and vinylidenes are terminal olefins, while the di- and tri-substituted vinylene olefins are internal olefins.

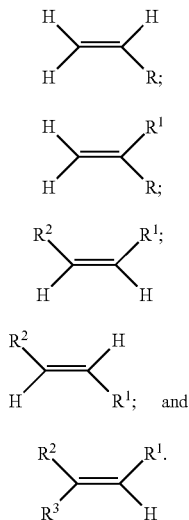

A uPAO can be partially or substantially completely hydrogenated in the presence of hydrogen and a hydrogenation catalyst to reduce the ethylenic unsaturation thereof and thereby obtaining a hydrogenated PAO. Such hydrogenated PAO can be more stable compared to the corresponding uPAO, offering higher thermal and oxidative resistance. A uPAO can be otherwise chemically modified to obtain a derivative thereof given the chemical reactivity of the ethylenic C=C double bond therein. The derivative can offer various interesting physical and chemical properties depending on the functional group attached to the carbon chain as a result of the modification.

As used herein, the term "lubricant" refers to a substance that can be introduced between two or more moving surfaces and to lower the level of friction between two adjacent surfaces moving relative to each other. A lubricant "base stock" is a material, typically a fluid at the operating temperature of the lubricant, used to formulate a lubricant by admixing with other components. Non-limiting examples of base stocks suitable in lubricants include API Group I, Group II, Group III, Group IV, Group V and Group VI base stocks. PAOs, particularly hydrogenated PAOs, have recently found wide use in lubricant formulations as Group IV base stocks.

NMR spectroscopy provides key structural information about the synthesized polymers. Proton NMR ($^1$H-NMR) analysis of the uPAO gives a quantitative breakdown of the olefinic structure types (i.e., vinyls, 1,2-di-substituted and tri-substituted vinylenes, and vinylidenes). In the present disclosure, compositions of mixtures of olefins comprising terminal olefins (vinyls and vinylidenes) and internal olefins (1,2-di-substituted vinylenes and tri-substituted vinylenes) are determined by using $^1$H-NMR. Specifically, a NMR instrument of at least a 500 MHz is run under the following conditions: a 30° flip angle RF pulse, 120 scans, with a delay of 5 seconds between pulses; sample dissolved in CDCl$_3$ (deuterated chloroform); and signal collection temperature at 25° C. The following approach is taken in determining the concentrations of the various olefins among all of the olefins from an NMR graph. First, peaks corresponding to different types of hydrogen atoms in vinyls (T1), vinylidenes (T2), 1,2-di-substituted vinylenes (T3), and tri-substituted vinylenes (T4) are identified at the peak regions in TABLE I below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, Ci=100*Qi/Qt).

TABLE I

| Type No. | Olefin Structure | Peak Region (ppm) | Peak Area | Number of Hydrogen Atoms | Quantity of Olefin (mol) | Concentration of Olefin (mol %) |
| --- | --- | --- | --- | --- | --- | --- |
| T1 | CH$_2$=CH—R$_1$ | 4.95-5.10 | A1 | 2 | Q1 = A1/2 | C1 |
| T2 | CH$_2$=CR$_1$R$_2$ | 4.70-4.84 | A2 | 2 | Q2 = A2/2 | C2 |
| T3 | CHR$_1$=CHR$_2$ | 5.31-5.55 | A3 | 2 | Q3 = A3/2 | C3 |
| T4 | CR$_1$R$_2$=CHR$_3$ | 5.11-5.30 | A4 | 1 | Q4 = A4 | C4 |

Carbon-13 NMR ($^{13}$C-NMR) is used to determine tacticity of the PAOs of the present invention. Carbon-13 NMR can be used to determine the concentration of the triads, denoted (m,m)-triads (i.e., meso, meso), (m,r)-(i.e., meso, racemic) and (r,r)-(i.e., racemic, racemic) triads, respectively. The concentrations of these triads defines whether the polymer is isotactic, atactic or syndiotactic. In the present disclosure, the concentration of the (m,m)-triads in mol % is recorded as the isotacticity of the PAO material. Spectra for a PAO sample are acquired in the following manner. Approximately 100-1000 mg of the PAO sample is dissolved in 2-3 ml of chloroform-d for $^{13}$C-NMR analysis. The samples are run with a 60 second delay and 90° pulse with at least 512 transients. The tacticity was calculated using the peak around 35 ppm (CH$_2$ peak next to the branch point). Analysis of the spectra is performed according to the paper by Kim, I.; Zhou, J.-M.; and Chung, H. Journal of Polymer Science: Part A: Polymer Chemistry 2000, 38 1687-1697. The calculation of tacticity is mm*100/(mm+mr+rr) for the molar percentages of (m,m)-triads, mr*100/(mm+mr+rr) for the molar percentages of (m,r)-triads, and rr*100/(mm+mr+rr) for the molar percentages of (r,r)-triads. The (m,m)-triads correspond to 35.5-34.55 ppm, the (m,r)-triads to 34.55-34.1 ppm, and the (r,r)-triads to 34.1-33.2 ppm.

II. Alkylated Anisole Compounds Useful for Base Stocks

The present disclosure relates to alkylated anisole compounds, which are useful in base stock compositions due to their increased thermal and oxidative stability, low volatility and viscosity as well as their good low temperature fluidity. In particular, alkylated anisole compounds are provided herein, which can be selectively synthesized from a uPAO and an anisole-derivative compound such that the anisole-derivative compound bonds predominately to a tertiary carbon of the uPAO. Thus, compounds having the formula (F-I) below are provided herein:

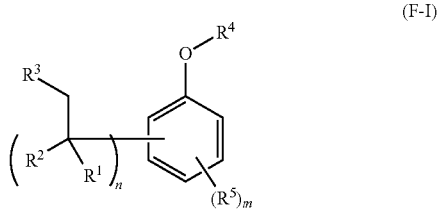

(F-I)

wherein $R^1$ and $R^2$ at each occurrence are independently a $C_1$-$C_{5000}$ alkyl group; $R^3$ at each occurrence is independently hydrogen or a $C_1$-$C_{5000}$ alkyl group; $R^4$ is a $C_1$-$C_{50}$ alkyl group or an unsubstituted or substituted phenyl group; $R^5$ at each occurrence is independently hydrogen or a $C_1$-$C_{30}$ alkyl group; n is 1, 2, 3, or 4; and m+n is 5.

In some embodiments, n may be 2, 3, or 4. In such variations, where n is 2, 3, or 4, each moiety comprising $R^1$, $R^2$, and $R^3$ may be bonded to the phenyl moiety at any suitable location with respect to the —$OR^4$ moiety, namely at a para (p-), meta (m-), or ortho (o-) position with respect to the —O—$R^4$ moiety. Further, where n is 2, 3 or 4, it is understood herein that each $R^1$, $R^2$, and $R^3$ in each moiety may be the same or different.

In other embodiments, n may be 1. In such variations where n is 1, it is understood herein that the moiety comprising $R^1$, $R^2$, and $R^3$ may be bonded to the phenyl moiety at any suitable location with respect to the —O—$R^4$ moiety, namely at a para (p-), meta (m-), or ortho (o-) position with respect to the —O—$R^4$ moiety. In particular, where n is 1, the moiety comprising $R^1$, $R^2$, and $R^3$ may be bonded to the phenyl moiety at a position para to the —O—$R^4$ moiety.

In one embodiment, an $R^3$ may be hydrogen, e.g., when a uPAO used during synthesis is a vinylidene olefin. In particular, where n is 1, $R^3$ may be hydrogen.

Alternatively, an $R^3$ may be a $C_1$-$C_{5000}$ alkyl group, a $C_1$-$C_{4000}$ alkyl group, a $C_1$-$C_{3000}$ alkyl group, a $C_1$-$C_{2000}$ alkyl group, a $C_1$-$C_{1000}$ alkyl group, a $C_1$-$C_{900}$ alkyl group, a $C_1$-$C_{800}$ alkyl group, a $C_1$-$C_{700}$ alkyl group, a $C_1$-$C_{600}$ alkyl group, a $C_1$-$C_{500}$ alkyl group, a $C_1$-$C_{400}$ alkyl group, a $C_1$-$C_{300}$ alkyl group, a $C_1$-$C_{200}$ alkyl group, a $C_1$-$C_{100}$ alkyl group, a $C_1$-$C_{50}$ alkyl group, a $C_1$-$C_{30}$ alkyl group, or $C_1$-$C_{10}$ alkyl group. The alkyl group may be linear or branched. In particular, an $R^3$ may be a $C_1$-$C_{100}$ alkyl group.

In certain aspects, where n is 1, $R^3$ may be a $C_1$-$C_{5000}$ alkyl group, a $C_1$-$C_{4000}$ alkyl group, a $C_1$-$C_{3000}$ alkyl group, a $C_1$-$C_{2000}$ alkyl group, a $C_1$-$C_{1000}$ alkyl group, a $C_1$-$C_{900}$ alkyl group, a $C_1$-$C_{800}$ alkyl group, a $C_1$-$C_{700}$ alkyl group, a $C_1$-$C_{600}$ alkyl group, a $C_1$-$C_{500}$ alkyl group, a $C_1$-$C_{400}$ alkyl group, a $C_1$-$C_{300}$ alkyl group, a $C_1$-$C_{200}$ alkyl group, a $C_1$-$C_{100}$ alkyl group, a $C_1$-$C_{50}$ alkyl group, a $C_1$-$C_{30}$ alkyl group, or $C_1$-$C_{10}$ alkyl group. Preferably, where n is 1, $R^3$ may be a $C_1$-$C_{100}$ alkyl group.

Additionally or alternatively, $R^1$ and $R^2$ at each occurrence each independently may be a $C_1$-$C_{5000}$ alkyl group, a $C_1$-$C_{4000}$ alkyl group, a $C_1$-$C_{3000}$ alkyl group, a $C_1$-$C_{2000}$ alkyl group, a $C_1$-$C_{1000}$ alkyl group, a $C_1$-$C_{900}$ alkyl group, a $C_1$-$C_{800}$ alkyl group, a $C_1$-$C_{700}$ alkyl group, a $C_1$-$C_{600}$ alkyl group, a $C_1$-$C_{500}$ alkyl group, a $C_1$-$C_{400}$ alkyl group, a $C_1$-$C_{300}$ alkyl group, a $C_1$-$C_{200}$ alkyl group, a $C_1$-$C_{100}$ alkyl group, a $C_1$-$C_{50}$ alkyl group, a $C_1$-$C_{30}$ alkyl group, or $C_1$-$C_{10}$ alkyl group. In particular, $R^1$ and $R^2$ at each occurrence each independently may be a $C_1$-$C_{100}$ alkyl group. The alkyl group may be linear or branched.

In certain variations, $R^1$ and $R^2$ at each occurrence each independently may be a $C_1$-$C_{300}$ linear alkyl group, a $C_1$-$C_{00}$ linear alkyl group, a $C_1$-$C_{50}$ linear alkyl group, a $C_1$-$C_{30}$ linear alkyl group or $C_1$-$C_{10}$ linear alkyl group. In a particular embodiment, $R^1$ and $R^2$ at each occurrence may be the same or different and each independently may be a $C_1$-$C_{100}$ linear alkyl group or a $C_1$-$C_{30}$ linear alkyl group.

In another embodiment, an $R^1$ may be a $C_1$-$C_{100}$ linear alkyl group, a $C_1$-$C_{50}$ linear alkyl group, a $C_1$-$C_{30}$ linear alkyl group or $C_1$-$C_{10}$ linear alkyl group and an $R^2$ may be a $C_1$-$C_{500}$ linear or branched alkyl group, a $C_1$-$C_{300}$ linear or branched alkyl group, a $C_1$-$C_{100}$ linear or branched alkyl group, a $C_1$-$C_{50}$ linear or branched alkyl group, a $C_1$-$C_{30}$ linear or branched alkyl group or a $C_1$-$C_{10}$ linear or branched alkyl group, e.g., where a uPAO used during synthesis is formed from linear alpha-olefins and a metallocene catalyst as further described herein. In particular, an $R^1$ may be a $C_1$-$C_{30}$ linear alkyl group and an $R^2$ may be a $C_1$-$C_{500}$ linear or branched alkyl group.

In certain variations, where an $R^1$ or an $R^2$ may be a $C_3$-$C_{5000}$ branched alkyl group, an $R^2$ may have the following formula (F-II) below:

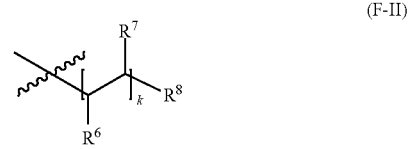

(F-II)

wherein: $R^6$ and $R^7$ at each occurrence are each independently a hydrogen or a $C_1$-$C_{30}$ linear alkyl group and k is a positive integer, provided however, among all of $R^6$ and $R^7$, at least one is a $C_1$-$C_{30}$ linear alkyl group; and $R^8$ is a hydrogen or a $C_1$-$C_{30}$ linear alkyl group. The positive integer, k, may be from 1 to 1000, 2 to 1000, 2 to 500, 2 to 100, 50 to 500, 50 to 200, 2 to 50, or 2 to 20. Preferably, k may be from 2 to 1000, 50 to 500 or 2 to 50.

In certain variations, $R^1$ or $R^2$ may be a $C_4$-$C_{5000}$ branched alkyl group represented by formula (F-II) above where n is larger than one (1), and at least 50% (e.g., at least 60%, 70%, 80%, 90%, or even 95%) of $R^6$ are hydrogen, and at least 50% (e.g., at least 60%, 70%, 80%, 90%, or even 95%) of $R^7$ are independently $C_1$-$C_{30}$ linear alkyl groups. In certain variations among these where a portion of $R^6$ and at least a portion of $R^7$ are alkyl groups, at least 80% of those $R^6$ that are alkyl groups are $C_1$-$C_4$ linear alkyl groups, and at least 80% of $R^7$ are $C_4$-$C_{30}$ linear alkyl groups. In certain variations, all of $R^6$ are hydrogen, and all of $R^7$ are independently $C_1$-$C_{30}$ linear alkyl groups. In certain variations, all of $R^6$ are hydrogen, and all of $R^7$ are identical $C_1$-$C_{30}$ linear alkyl groups.

In certain variations, $R^1$ or $R^2$ may be a $C_4$-$C_{5000}$ branched alkyl group represented by formula (F-II) above where n is larger than one (1), and at least 50% (e.g., at least 60%, 70%, 80%, 90%, or even 95%) of $R^7$ are hydrogen, and at least 50% (e.g., at least 60%, 70%, 80%, 90%, or even 95%) of $R^6$ are independently $C_1$-$C_{30}$ linear alkyl groups. In certain variations among these where a portion of $R^7$ and at least a portion of $R^6$ are alkyl groups, at least 80% of those $R^7$ that are alkyl groups are $C_1$-$C_4$ linear alkyl groups, and at least 80% of $R^6$ are $C_4$-$C_{30}$ linear alkyl groups. In certain variations, all of $R^7$ are hydrogen, and all of $R^6$ are independently $C_1$-$C_{30}$ linear alkyl groups. In certain variations, all of $R^7$ are hydrogen, and all of $R^6$ are identical $C_1$-$C_{30}$ linear alkyl groups.

Additionally or alternatively, $R^4$ may be a $C_1$-$C_{50}$ alkyl group, a $C_1$-$C_{300}$ alkyl group, a $C_1$-$C_{100}$ alkyl group, a $C_1$-$C_{50}$ alkyl group, a $C_1$-$C_{30}$ alkyl group or a $C_1$-$C_{10}$ alkyl group. The alkyl group may be linear or branched. In particular, $R^4$ may be a $C_1$-$C_{50}$ alkyl group, more particularly, a $C_1$-$C_{50}$ linear alkyl group or a $C_1$-$C_{30}$ linear alkyl group.

Additionally or alternatively, $R^4$ may be an unsubstituted or substituted phenyl group. For example, the phenyl group may be substituted with one or more $C_1$-$C_{50}$ alkyl groups, preferably, one or more $C_1$-$C_{30}$ alkyl groups, or more preferably, one or more $C_1$-$C_{10}$ alkyl groups.

Additionally or alternatively, $R^5$ may be hydrogen.

In one embodiment, n may be 1, $R^1$ and $R^2$ may independently be a $C_1$-$C_{100}$ alkyl group or a $C_1$-$C_{30}$ alkyl group, $R^3$ may be hydrogen or a $C_1$-$C_{100}$ alkyl group, $R^4$ may be a $C_1$-$C_{50}$ alkyl group, and $R^5$ may be hydrogen.

Additionally or alternatively, $R^5$ may be a $C_1$-$C_{30}$ alkyl group, a $C_1$-$C_{10}$ alkyl group, a $C_1$-$C_4$ alkyl group or a $C_1$-$C_2$ alkyl group. The alkyl group may be linear or branched. It is understood herein that $R^5$ may be bonded to the phenyl moiety at any suitable location with respect to the —O—$R^4$ moiety, namely the para (p-), meta (m-), or ortho (o-) position with respect to the —O—$R^4$ moiety.

Examples of compounds of formula (F-I) are shown below in TABLE II.

TABLE II

Exemplary Compounds of Formula (F-I)

(1)

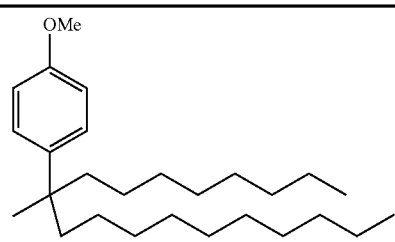

1-methoxy-4-(9-methylnonadecan-9-yl)benzene (2)

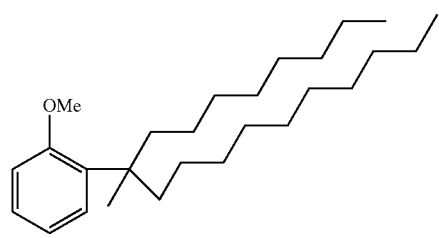 [SMILES: CCCCCCCCCCC(C)(CCCCCCCC)c1ccccc1OC]

1-methoxy-2-(9-methylnonadecan-9-yl)benzene

TABLE II-continued

Exemplary Compounds of Formula (F-I)

(3)

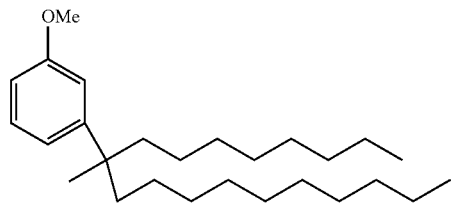 [SMILES: CCCCCCCCCCC(C)(CCCCCCCC)c1cccc(OC)c1]

1-methoxy-3-(9-methylnonadecan-9-yl)benzene

The compounds of formula (F-I) described herein may have various levels of regio-regularity. For example, each compound of formula (F-I) may be substantially atactic, isotactic, or syndiotactic. The compounds, however, can be a mixture of different molecules, each of which can be atactic, isotactic, or syndiotactic. Without intending to be bound by a particular theory, however, it is believed that regio-regular molecules, especially the isotactic ones, due to the regular distribution of the pendant groups, especially the longer ones, tend to contribute to increased performance (e.g., electrohydrodynamic lubrication performance) of base stocks comprising those compounds of formula (F-I) described herein. Thus, it is preferred that at least about 50 mol %, or at least about 60 mol %, or at least about 70 mol %, or at least about 75 mol %, or at least about 80 mol %, or at least about 90 mol %, or even about 95 mol % of the compounds of formula (F-I) described herein are regio-regular. It is further preferred that at least about 50 mol %, or at least about 60 mol %, or at least about 70 mol %, or at least about 75 mol %, or at least about 80 mol %, or at least about 90 mol %, or even about 95 mol %, of compounds of formula (F-I) described herein are isotactic.

III. Processes for Making the Alkylated Anisole Compounds

Processes for making the compounds of formula (F-I) are provided herein. In particular, the process comprises reacting a compound having the following formula (F-Ia):

(F-Ia)

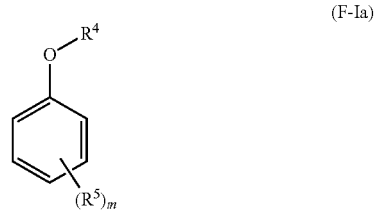

with an olefin-containing material comprising a compound having the following formula (F-Ib):

(F-Ib)

in the presence of an acid catalyst, wherein $R^1$, $R^2$, $R^3$, $R^4$ and m are as described above in association with formula (F-I).

As described herein, alkylated anisoles of formula (F-I) can be selectively synthesized from a uPAO (formula (F-Ib)) and an anisole-derivative compound (formula (F-Ia)) in the presence of an acid catalyst such that the anisole-derivative compound bonds to a tertiary carbon of the uPAO. Thus, advantageously, the process described herein has a high selectivity for producing compounds that correspond in structure to formula (F-I). For example, at least about 50 mol %, at least about 60 mol %, at least about 70 mol %, at least about 80 mol %, at least about 90 mol %, at least about 95 mol % or about 99 mol % of the compounds produced correspond in structure to formula (F-I). Additionally or alternatively, about 50 mol % to about 99 mol %, about 70 mol % to about 99 mol %, about 80 mol % to about 99 mol %, or about 90 mol % to about 99 mol % of the compounds produced correspond in structure to formula (F-I). Theoretically, even if this reaction has a lower selectivity than 90 mol %, one can nonetheless purify the product mixture to obtain a final product having higher than 90 mol % of purity of the intended product. In some instances, the balance of the alkylated anisoles formed have the anisole-derivative compound bonded to a primary or secondary carbon of the uPAO.

Further, the process described herein has a high selectivity for producing compounds corresponding in structure to formula (F-I) wherein the moiety comprising $R^1$, $R^2$, and $R^3$ may be bonded to the phenyl ring at position para to the —O—$R^4$ moiety. For example, at least about 70 mol %, at least about 80 mol %, at least about 90 mol %, at least about 95 mol % or about 99 mol % of the compounds produced correspond in structure to formula (F-I) where the moiety comprising $R^1$, $R^2$, and $R^3$ is bonded to the phenyl ring at position para to the —O—$R^4$ moiety. Additionally or alternatively, about 70 mol % to about 99 mol %, about 80 mol % to about 99 mol %, or about 90 mol % to about 99 mol % of the compounds produced correspond in structure to formula (F-I) where the moiety comprising $R^1$, $R^2$, and $R^3$ is bonded to the phenyl ring at position para to the —O—$R^4$ moiety.

Additionally or alternatively, the process described herein may have a high selectivity for producing compounds corresponding in structure to formula (F-I), which are mono-alkylated (i.e., where n is 1). For example, at least about 70 mol %, at least about 80 mol %, at least about 90 mol %, at least about 95 mol % or about 99 mol % of the compounds produced correspond in structure to formula (F-I) n is 1. Additionally or alternatively, about 70 mol % to about 99 mol %, about 80 mol % to about 99 mol %, or about 90 mol % to about 99 mol % of the compounds produced correspond in structure to formula (F-I) where n is 1.

In various aspects, $R^3$ may be hydrogen. In some instances, the olefin-containing material may comprise one or more olefin compounds of formula (F-Ib), where $R^3$ is hydrogen, in an amount of at least about 1.0 wt %, at least about 10 wt %, at least about 20 wt %, at least about 30 wt %, at least about 40 wt %, at least about 50 wt %, at least about 60 wt %, at least about 70 wt %, at least about 75 wt %, at least about 80 wt %, at least about 90 wt %, at least about 99 wt %, or about 100 wt % based on the total weight of the olefin-containing material. In particular, the olefin-containing material may comprise one or more olefin compounds of formula (F-Ib), where $R^3$ is hydrogen, in an amount of at least about 75 wt %. Additionally or alternatively, the olefin-containing material may comprise a compound of formula (F-Ib), where $R^3$ is hydrogen, in an amount of about 1.0 wt % to about 100 wt %, 1.0 wt % to about 90 wt %, about 20 wt % to about 90 wt %, about 40 wt % to about 90 wt %, about 50 wt % to about 90 wt %, about 60 wt % to about 90 wt %, about 75 wt % to about 90 wt % or about 80 wt % to about 90 wt %.

Alternatively, $R^3$ may be a $C_1$-$C_{5000}$ alkyl group, a $C_1$-$C_{4000}$ alkyl group, a $C_1$-$C_{3000}$ alkyl group, a $C_1$-$C_{2000}$ alkyl group, a $C_1$-$C_{1000}$ alkyl group, a $C_1$-$C_{900}$ alkyl group, a $C_1$-$C_{800}$ alkyl group, a $C_1$-$C_{700}$ alkyl group, a $C_1$-$C_{600}$ alkyl group, a $C_1$-$C_{500}$ alkyl group, a $C_1$-$C_{400}$ alkyl group, a $C_1$-$C_{300}$ alkyl group, a $C_1$-$C_{200}$ alkyl group, a $C_1$-$C_{100}$ alkyl group, a $C_1$-$C_{50}$ alkyl group, a $C_1$-$C_{30}$ alkyl group, or $C_1$-$C_{10}$ alkyl group. In particular, $R^3$ may be a $C_1$-$C_{100}$ alkyl group. In some instances, the olefin-containing material may comprise one or more compounds of formula (F-Ib), where $R^3$ is an alkyl group (e.g., $C_1$-$C_{100}$ alkyl group), in an amount of at least about 1.0 wt %, at least about 10 wt %, at least about 20 wt %, at least about 25 wt %, at least about 30 wt %, at least about 40 wt %, at least about 50 wt %, at least about 60 wt %, at least about 70 wt %, at least about 75 wt %, at least about 80 wt %, at least about 90 wt %, at least about 99 wt %, or about 100 wt % based on the total weight of the olefin-containing material. In particular, the olefin-containing material may comprise a compound of formula (F-Ib), where $R^3$ is an alkyl group (e.g., $C_1$-$C_{100}$ alkyl group) in an amount of at least about 50 wt %. Additionally or alternatively, the olefin-containing material may comprise a compound of formula (F-Ib), where $R^3$ is an alkyl group (e.g., $C_1$-$C_{100}$ alkyl group), in an amount of about 1.0 wt % to about 100 wt %, 1.0 wt % to about 90 wt %, about 10 wt % to about 60 wt %, about 10 wt % to about 50 wt %, about 10 wt % to about 40 wt % or about 10 wt % to about 25 wt %.

In some embodiments, the olefin-containing material may comprise a mixture of compounds of formula (F-Ib). For example, the olefin-containing material may comprise a mixture of: (i) one or more olefin compounds of formula (F-Ib) wherein $R^3$ is hydrogen; and (ii) one or more olefin compounds of formula (F-Ib) wherein $R^3$ is an alkyl group (e.g., $C_1$-$C_{100}$ alkyl group). In some embodiments, the olefin-containing material may comprise a mixture of: (i) about 1.0 wt % to about 99 wt % of one or more olefin compounds of formula (F-Ib) wherein $R^3$ is hydrogen; and (ii) about 1.0 wt % to about 99 wt % of one or more olefin compounds of formula (F-Ib) wherein $R^3$ is an alkyl group (e.g., $C_1$-$C_{100}$ alkyl group). In particular, the olefin-containing material may comprise a mixture of: (i) about 50 wt % to about 90 wt % or about 75 wt % to about 90 wt % of one or more olefin compounds of formula (F-Ib) wherein $R^3$ is hydrogen; and (ii) about 10 wt % to about 50 wt % or about 10 wt % to about 25 wt % of one or more olefin compounds of formula (F-Ib) wherein $R^3$ is an alkyl group (e.g., $C_1$-$C_{100}$ alkyl group).

The olefin-containing materials used in the process may be PAO (mPAO, cPAO, and mixtures thereof) dimers ($C_4$-$C_{100}$), trimers ($C_6$-$C_{100}$), tetramers ($C_1$-$C_{100}$) and higher oligomers, pentamer, hexamer, and the like, or alpha-olefins (e.g., $C_2$-$C_{30}$ alpha-olefin). Suitable alpha-olefins include, for example, alkyl olefins such as 1-hexene, 1-octene, 1-decene, 1-dodecene, 1-tetradecene, 1-octadecene, and the like.

The PAO dimer (e.g., mPAO, cPAO) can be any dimer with terminal C=C double bond prepared by using metallocene or other single-site catalyst. The dimer can be from an alpha-olefin (e.g., $C_2$-$C_{30}$ alpha-olefin), for example, 1-hexene, 1-octene, 1-decene, 1-dodecene, 1-tetradecene, 1-octadecene or a combination of alpha-olefins. In particular, the olefin-containing material in the process provided herein may be produced by oligomerization of a $C_1$-$C_{100}$ alpha-olefin in the presence of a metallocene compound. Metallocene-catalyzed alpha-olefin oligomerization processes are described in U.S. Pat. Nos. 5,688,887 and 6,043,401 and WO 2007/011973, each of which is incorporated herein by reference in its entirety and to which reference is made for details of feeds, metallocene catalysts, process conditions and characterizations of products.

In some examples, at least about 50 mol %, or at least about 60 mol %, or at least about 70 mol %, or at least about 75 mol %, or at least about 80 mol %, or at least about 90 mol %, or even about 95 mol %, of the olefin-containing materials described herein are isotactic. In particular, at least about 60 mol %, or at least about 75 mol %, or at least about 80 mol % of the olefin-containing materials described herein are isotactic.

The cPAOs may be made by using conventional catalysts to form olefin-containing material having a formula (F-Ib). Examples of suitable conventional catalysts include but are not limited to Lewis acid compounds, such as BF3, AlCl3, aluminum trialkyls, or combinations thereof. When using conventional catalysts, the resultant olefin-containing material tends to be a mixture of olefin compounds with highly varied $R^1$, $R^2$, and $R^3$. At least one of $R^1$, $R^2$ and $R^3$ may be an alkyl group having a carbon backbone chain with multiple pendant groups attached thereto, many of which are short-chain alkyl groups such as methyl, ethyl, and the like. The distribution of such pendant groups on the backbone chain can be random. Such unhydrogenated cPAOs obtained by using conventional catalysts typically may be atactic. Processes for the production of cPAOs are disclosed, for example, in the following patents, each of which is incorporated herein by reference in its entirety: U.S. Pat. Nos. 3,149,178; 3,382,291; 3,742,082; 3,769,363; 3,780,128; 4,172,855; and 4,956,122; as well as in Shubkin, R. L. (Ed.) (1992) Synthetic Lubricants and High-Performance Functional Fluids (Chemical Industries) New York: Marcel Dekker Inc.

PAO lubricant compositions in which little double bond isomerization is found has resulted in different classes of high viscosity index PAO (HVI-PAO), which are also contemplated for use herein. In one class of HVI-PAO, a reduced chromium catalyst is reacted with an alpha-olefin monomer. Such PAOs are described in U.S. Pat. Nos. 4,827,073; 4,827,064; 4,967,032; 4,926,004; and 4,914,254, each of which is incorporated herein by reference in its entirety.

As described herein, $R^4$ may be an alkyl group (e.g., a $C_1$-$C_{50}$ alkyl group, a $C_1$-$C_{40}$ alkyl group, a $C_1$-$C_{30}$ alkyl group, a $C_1$-$C_{20}$ alkyl group, a $C_1$-$C_{10}$ alkyl group, a $C_1$-$C_8$ alkyl group, etc.). Further, $R^5$ may be hydrogen or an alkyl group as described herein (e.g., a $C_1$-$C_{50}$ alkyl group, a $C_1$-$C_{40}$ alkyl group, a $C_1$-$C_{30}$ alkyl group, a $C_1$-$C_{20}$ alkyl group, a $C_1$-$C_{10}$ alkyl group, a $C_1$-$C_8$ alkyl group, a $C_1$-$C_4$ alkyl group, a $C_1$-$C_2$ alkyl group).

Suitable acid catalysts that can be used in the processes described herein for making the compound having formula (F-I) include, for example, a Lewis acid. The Lewis acid catalysts useful for coupling reactions include metal and metalloid halides conventionally used as Friedel-Crafts catalysts. Suitable examples include AlCl3, BF3, AlBr3, TiCl3, and TiCl4, either as such or with a protic promoter. Other examples include solid Lewis acid catalysts; acid clays; polymeric acidic resins; amorphous solid catalysts, such as silica-alumina; and heteropoly acids, such as the tungsten zirconates, tungsten molybdates, tungsten vanadates, phosphotungstates and molybdotungstovanadogermanates (e.g. $WO_x/ZrO_2$ and $WO_x/MoO_3$). Beside these catalysts, acidic ionic liquid can also be used as catalysts for coupling reactions. Among different catalysts polymeric acidic resins, such as Amberlyst 15 and Amberlyst 36 are most preferred. In particular, the acid catalyst may be a solid acid catalyst selected from the group consisting of a solid Lewis acid, an acid clay, a polymeric acidic resin, silica-alumina, a mineral acid and a combination thereof. Examples of suitable mineral acids include, but are not limited to hydrochloric acid (HCl), hydrobromic acid (HBr), hydrofluoric acid (HF), sulfuric acid ($H_2SO_4$), phosphoric acid ($H_3PO_4$), nitric acid ($HNO_3$) and combinations thereof.

Other suitable acid catalysts include molecular sieve materials, such as synthetic or natural zeolites. For example, the acid catalyst may comprise a molecular sieve having a framework structure selected from the group consisting of BEA, EUO, FAU, FER, HEU, MEL, MFI, MOR, MRE, MTW, MTT, MWW, OFF, and combinations thereof. Examples of molecular sieve materials having such a framework structure include, but are not limited to ZSM-5, ZSM-11, ZSM-12, ZSM-23, ZSM-35, ZSM-48, ZSM-50, Zeolite Beta, MCM-56, MCM-22, MCM-36, MCM-49, zeolite Y, zeolite X, and combinations thereof. In particular, the acid catalyst may comprise MCM-49 or zeolite Y.

A person of ordinary skill in the art knows how to make the aforementioned frameworks and molecular sieves. For example, see the references provided in the International Zeolite Association's database of zeolite structures found at www.iza-structure.org/databases.

Typically, the amount of acid catalyst used is 0.1 to 30 weight % and preferably 0.2 to 5 weight % based on total weight of the feed.

Reaction conditions for the process described herein, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to about 175° C. The reaction may be carried out under ambient pressure and the contact time may vary from a matter of seconds or minutes to a few hours or greater. The reactants can be added to the reaction mixture or combined in any order. The stir time employed can range from 0.5 to 48 hours, preferably from 1 to 36 hours, and more preferably from 2 to 24 hours.

IV. Lubricant Oil and Base Stock Compositions

This disclosure provides lubricating oils useful as engine oils and in other applications characterized by excellent stability, solvency and dispersancy characteristics. The lubricating oils are based on high quality base stocks including a major portion comprising one or more compounds corresponding in structure to formula (F-1) as described herein. Alternatively, base stocks including a major portion of other components, such as a Group I, II and/or III mineral oil base stocks, GTL, Group IV (e.g., PAO), Group V (e.g., esters, alkylated aromatics, PAG) and combinations thereof, and a minor portion comprising one or more compounds corresponding in structure to formula (F-1) as described herein as a co-base stock are also provided herein. The lubricating oil base stock can be any oil boiling in the lube oil boiling range, typically between about 100 to about 450° C. In the present specification and claims, the terms base oil(s) and base stock(s) are used interchangeably.

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine. Thus high VI (HVI) oil has performance advantages in both high and low temperature operation. VI is determined according to ASTM method D 2270-93 [1998]. VI is related to kinematic viscosities measured at 40° C. and 100° C. using ASTM Method D 445-01.

IV.A. Lubricating Oil Base Stocks

A wide range of lubricating oils is known in the art. Lubricating oils that are useful in the present disclosure are both natural oils and synthetic oils. Natural and synthetic oils (or mixtures thereof) can be used unrefined, refined, or re-refined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve the at least one lubricating oil property. One skilled in the art is familiar with many purification processes. These processes include solvent extraction, secondary distillation, acid extraction, base extraction, filtration, and percolation. Re-refined oils are obtained by processes analogous to refined oils but using an oil that has been previously used as a feed stock.

Groups I,II, III, IV and V are broad categories of base oil stocks developed and defined by the American Petroleum Institute (API Publication 1509; www.API.org) to create guidelines for lubricant base oils. Group I base stocks generally have a viscosity index of from 80 to 120 and contain greater than 0.03% sulfur and less than 90% saturates. Group II base stocks generally have a viscosity index of from 80 to 120, and contain less than or equal to 0.03% sulfur and greater than or equal to 90% saturates. Group III stock generally has a viscosity index greater than 120 and contains less than or equal to 0.03% sulfur and greater than 90% saturates. Group IV includes polyalpha-olefins (PAO). Group V base stocks include base stocks not included in Groups I-IV. TABLE III below summarizes properties of each of these five groups.

TABLE III

| Base Oil Properties | | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |

TABLE III-continued

| Base Oil Properties | | | |
|---|---|---|---|
| | Saturates | Sulfur | Viscosity Index |
| Group III | ≥90 and | ≤0.03% and | ≥120 |
| Group IV | | Includes PAO products | |
| Group V | | All other base oil stocks not included in Groups I, II, III or IV | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Group II and/or Group III hydroprocessed or hydrocracked base stocks, as well as synthetic oils such as poly-alpha-olefins, alkyl aromatics and synthetic esters, i.e. Group IV and Group V oils are also well known base stock oils.

Synthetic oils include hydrocarbon oil such as polymerized and interpolymerized olefins (polybutyl ones, polypropylenes, propylene isobutylene copolymers, ethylene-olefin copolymers, and ethylene-alpha-olefin copolymers, for example). PAO oil base stocks, the Group IV API base stocks, are a commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073, which are incorporated herein by reference in their entirety. Group IV oils, that is, the PAO base stocks have viscosity indices preferably greater than 130, more preferably greater than 135, still more preferably greater than 140.

In one particular embodiment, a lubricant base stock is provided. The lubricant base stock may comprise one or more of the compounds of formula (F-I) as described herein. Also contemplated herein, are formulated lubricant oil compositions comprising one or more of the lubricant base stocks described herein.

As discussed herein, the compounds of formula (F-I) unexpectedly have a combination of desirable properties. For example, compositions comprising compounds of formula (F-I), e.g., lubricant base stock compositions provided herein, may have a rotating pressure vessel oxidation test (RPVOT) break time, measured according to ASTM standard D-2272, of at least about 200 minutes, at least about 300 minutes, at least about 400 minutes, at least about 500 minutes, at least about 600 minutes, at least about 700 minutes, at least about 800 minutes, at least about 850 minutes, at least about 900 minutes or about 1000 minutes. Additionally or alternatively, compositions comprising compounds of formula (F-I), e.g., lubricant base stock compositions provided herein, may have an RPVOT break time of about 200 to about 1000 minutes, about 200 to about 900 minutes, about 300 to about 900 minutes, or about 300 to about 800 minutes.

Further, compositions comprising compounds of formula (F-I), e.g., lubricant base stock compositions provided herein, may have a kinematic viscosity at 100° C. (KV100), measured according to ASTM standard D-445, from about 1 to about 20 cSt, from about 1 to about 15 cSt, preferably from about 2 to about 10 cSt, preferably from about 2 to about 5.5 cSt, or more preferably from about 5 to about 5.5 cSt.

Additionally or alternatively, compositions comprising compounds of formula (F-I), e.g., lubricant base stock compositions provided herein, may have a kinematic viscosity at 40° C. (KV40), measured according to ASTM standard D-445, from about 10 to about 100 cSt, from about 10 to about 50 cSt, preferably from about 20 to about 40 cSt, and more preferably from about 20 to about 30 cSt.

Additionally or alternatively, compositions comprising compounds of formula (F-I), e.g., lubricant base stock compositions provided herein, may have a viscosity index (VI), measured according to ASTM standard D-2270, from about 25 to about 200, preferably from about 50 to about 200, and more preferably from about 70 to about 200.

Additionally or alternatively, compositions comprising compounds of formula (F-I), e.g., lubricant base stock compositions provided herein, may have a Noack volatility of no greater than about 25%, preferably no greater than about 20%, and more preferably no greater than about 18%. As used herein, Noack volatility is determined by ASTM D-5800.

Additionally or alternatively, compositions comprising compounds of formula (F-I), e.g., lubricant base stock compositions provided herein, may have a pour point), measured according to ASTM standard D-5950, of about 0.0° C., less than about −10° C., less than about −20° C., less than about −30° C., less than about −40° C., less than about −45° C., less than about −50° C., less than about −55° C., less than about −60° C. or −70° C. Preferably, the compositions provided herein may have a pour point of less than about −55° C. The compositions provided herein may have a pour point of about −70° C. to about 0.0° C., about −70° C. to about −10° C., about −70° C. to about −20° C., about −70° C. to about −30° C., about −70° C. to about −40° C., about −70° C. to about −45° C., or about −70° C. to about −50° C.

Additionally or alternatively, compositions comprising compounds of formula (F-I), e.g., lubricant base stock compositions provided herein, may have a Brookfield viscosity at −40° C., measured according to ASTM standard D-2983, from about 10000 to about 30000 cP, preferably from about 15000 to about 25000 cP, and more preferably from about 17,500 to about 22,500 cP.

Additionally or alternatively, compositions comprising compounds of formula (F-I), e.g., lubricant base stock compositions provided herein, may have one or more of the following:
  (i) a hydrolytic stability, measured according to ASTM D-2619, of about 0.1 to about 1.0 mg KOH/g or about 0.1 to about 0.5 mg KOH/g;
  (ii) a low foaming tendency, measured according to ASTM D-892, at least lower than alkylated naphthalene base stocks; and
  (iii) a solubility, measured according to Fedors Correlation, of about 8 to about 10 d(i) at 25° C. (cal/cc)^1/2.

Compositions comprising compounds of formula (F-I), e.g., lubricant base stock compositions provided herein, may have two of (i)-(iii) (e.g., (i) and (ii), (i) and (iii), (ii) and (iii)) or all three of (i)-(iii).

Esters in a minor amount may be useful in the lubricating oils of this disclosure. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols such as the neopentyl polyols; e.g., neopentyl glycol, trimethylol ethane, 2-methyl-2-propyl-1,3-propanediol, trimethylol propane, pentaerythritol and dipentaerythritol with alkanoic acids containing at least 4 carbon atoms, preferably $C_5$ to $C_{30}$ acids such as saturated straight chain fatty acids including caprylic acid, capric acids, lauric acid, myristic acid, palmitic acid, stearic acid, arachic acid, and behenic acid, or the corresponding branched chain fatty acids or unsaturated fatty acids such as oleic acid, or mixtures of any of these materials.

Esters should be used in an amount such that the improved wear and corrosion resistance provided by the lubricating oils of this disclosure are not adversely affected.

Non-conventional or unconventional base stocks and/or base oils include one or a mixture of base stock(s) and/or base oil(s) derived from: (1) one or more Gas-to-Liquids (GTL) materials, as well as (2) hydrodewaxed, or hydroisomerized/cat (and/or solvent) dewaxed base stock(s) and/or base oils derived from synthetic wax, natural wax or waxy feeds, mineral and/or non-mineral oil waxy feed stocks such as gas oils, slack waxes (derived from the solvent dewaxing of natural oils, mineral oils or synthetic oils; e.g., Fischer-Tropsch feed stocks), natural waxes, and waxy stocks such as gas oils, waxy fuels hydrocracker bottoms, waxy raffinate, hydrocrackate, thermal crackates, foots oil or other mineral, mineral oil, or even non-petroleum oil derived waxy materials such as waxy materials recovered from coal liquefaction or shale oil, linear or branched hydrocarbyl compounds with carbon number of 20 or greater, preferably 30 or greater and mixtures of such base stocks and/or base oils.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL base stocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL base stock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce tube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL base stock(s) and/or base oil(s) derived from GTL materials, especially, hydrodewaxed or hydroisomerized/ followed by cat and/or solvent dewaxed wax or waxy feed, preferably F-T material derived base stock(s) and/or base oil(s), are characterized typically as having kinematic viscosities at 100° C. of from 2 $mm^2/s$ to 50 $mm^2/s$ (ASTM D445). They are further characterized typically as having pour points of −5° C. to −40° C. or lower (ASTM D97). They are also characterized typically as having viscosity indices of 80 to 140 or greater (ASTM D2270).

In addition, the GTL base stock(s) and/or base oils) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) typically have very low sulfur and nitrogen content, generally containing less than 10 ppm, and more typically less than 5 ppm of each of these elements. The sulfur and nitrogen content of GTL base stock(s) and/or base oil(s) obtained from F-T material, especially F-T wax, is essentially nil. In addition, the absence of phosphorous and aromatics make this materially especially suitable for the formulation of low SAP products.

The term GTL base stock and/or base oil and/or wax isomerate base stock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL base stock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, Group V and Group VI oils and mixtures thereof, preferably API Group II, Group III, Group IV, Group V and Group VI oils and mixtures thereof, more preferably the Group III to Group VI base oils due to their exceptional volatility, stability, viscometric and cleanliness features. Minor quantities of Group I stock, such as the amount used to dilute additives for blending into formulated lube oil products, can be tolerated but should be kept to a minimum, i.e. amounts only associated with their use as diluent/carrier oil for additives used on an "as received" basis. Even in regard to the Group II stocks, it is preferred that the Group II stock be in the higher quality range associated with that stock, i.e. a Group II stock having a viscosity index in the range 100<VI<120.

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) and hydrodewaxed, or hydroisomerized/cat (and/or solvent) dewaxed base stock(s) and/or base oil(s) typically have very low sulfur and nitrogen content, generally containing less than 10 ppm, and more typically less than 5 ppm of each of these elements. The sulfur and nitrogen content of GTL, base stock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

The lubricating oils are based on high quality base stocks including a major portion comprising one or more compounds corresponding in structure to formula (F-1) as described herein. Alternatively, base stocks including a major portion of other components, such as a Group I, II and/or III mineral oil base stocks, GTL, Group IV (e.g., PAO), Group V (e.g., esters, alkylated aromatics, PAG), and minor portion comprising one or more compounds corresponding in structure to formula (F-1) as described herein as a co-base stock are also provided herein.

As stated above, lubricant base stocks comprising one or more compounds corresponding in structure to formula (F-1) as described herein may be present in lubricating oil compositions as a primary component lubricant base stock or a minor lubricant co-base stock component. Thus, the formulated lubricant compositions disclosed herein may comprise the lubricant base stock in an amount from about 1 wt % to about 99 wt % or about 5 wt % to about 90 wt %. For example, when present as a primary component, the lubricant base stock described herein may be present in lubricating oils from about 50 wt % to about 99 wt % of the total composition (all proportions and percentages set out in this specification are by weight unless the contrary is stated) and more usually in the range of about 80 wt % to about 99 wt % or about 80 wt % to about 90 wt %. Alternatively, when present as a minor co-base stock component, the lubricant base stock described herein may be present in lubricating oils from about 1 wt % to about 50 wt % of the total composition (all proportions and percentages set out in this specification are by weight unless the contrary is stated), preferably from about 5 wt % to about 30 wt % and more preferably from about 10 wt % to about 20 wt %.

IV.B. Additives

The formulated lubricating oil useful in the present disclosure may additionally contain one or more of the other commonly used lubricating oil performance additives including but not limited to dispersants, other detergents, corrosion inhibitors, rust inhibitors, metal deactivators, other anti-wear agents and/or extreme pressure additives, antiseizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

The types and quantities of performance additives used in combination with the instant disclosure in lubricant compositions are not limited by the examples shown herein as illustrations.

IV.C. Viscosity Improvers

Viscosity improvers (also known as Viscosity Index modifiers, and VI improvers) increase the viscosity of the oil composition at elevated temperatures which increases film thickness, while having limited effect on viscosity at low temperatures.

Suitable viscosity improvers include high molecular weight hydrocarbons, polyesters and viscosity index improver dispersants that function as both a viscosity index improver and a dispersant. Typical molecular weights of these polymers are from 10,000 to 1,000,000, more typically 20,000 to 500,000, and even more typically between 50,000 and 200,000.

Examples of suitable viscosity improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The amount of viscosity modifier may range from zero to 8 wt %, preferably zero to 4 wt %, more preferably zero to 2 wt % based on active ingredient and depending on the specific viscosity modifier used.

IV.D. Antioxidants

Typical antioxidant include phenolic antioxidants, aminic antioxidants and oil-soluble copper complexes. Detailed description of such antioxidants and their quantities of use can be found, e.g., in WO 2015/060984 A1, the relevant portions thereof are incorporated herein by referene in their entirety.

IV.E. Detergents

In addition to the alkali or alkaline earth metal salicylate detergent which is an essential component in the present disclosure, other detergents may also be present. While such other detergents can be present, it is preferred that the amount employed be such as to not interfere with the synergistic effect attributable to the presence of the salicylate. Therefore, most preferably such other detergents are not employed.

If such additional detergents are present, they can include alkali and alkaline earth metal phenates, sulfonates, carboxylates, phosphonates and mixtures thereof. These supplemental detergents can have total base number (TBN) ranging from neutral to highly overbased, i.e. TBN of 0 to over 500, preferably 2 to 400, more preferably 5 to 300, and they can be present either individually or in combination with each other in an amount in the range of from 0 to 10 wt %, preferably 0.5 to 5 wt % (active ingredient) based on the total weight of the formulated lubricating oil. As previously stated, however, it is preferred that such other detergent not be present in the formulation.

Such additional other detergents include by way of example and not limitation calcium phenates, calcium sulfonates, magnesium phenates, magnesium sulfonates and other related components (including borated detergents).

IV.F. Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the alkenylsuccinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary patents describing such dispersants are U.S. Pat. Nos. 3,172,892; 3,219,666; 3,316,177 and 4,234,435. Other types of dispersants are described in U.S. Pat. Nos. 3,036,003; and 5,705,458.

Hydrocarbyl-substituted succinic acid compounds are popular dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between alkenyl succinic anhydrides and amines. Molar ratios can vary depending on the amine or polyamine. For example, the molar ratio of alkenyl succinic anhydride to TEPA can vary from 1:1 to 5:1.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from 0.1 to 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from 800 to 2,500.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and di-amino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N-(Z-NH-)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Preferred dispersants include borated and non-borated succinimides, including those derivatives from mono-succinimides, leis-succinimides, and/or mixtures of mono- and bis-succinimides, wherein the hydrocarbyl succinimide is derived from a hydrocarbylene group such as polyisobutylene having a Mn of from 500 to 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of 0.1 to 20 wt %, preferably 0.1 to 8 wt %, more preferably 1 to 6 wt % (on an as-received basis) based on the weight of the total lubricant.

IV.G. Pour Point Depressants

Conventional pour point depressants (also known as lube oil flow improvers) may also be present. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of 0.0 to 0.5 wt %, preferably 0 to 0.3 wt %, more preferably 0.001 to 0.1 wt % on an as-received basis.

IV.H. Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles thiadiazoles and mixtures thereof. Such additives may be used in an amount of 0.01 to 0.5 wt %, preferably 0.01 to 1.5 wt %, more preferably 0.01 to 0.2 wt %, still more preferably 0.01 to 0.1 wt % (on an as-received basis) based on the total weight of the lubricating oil composition.

IV.I. Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of 0.01 to 3 wt %, preferably 0.01 to 2 wt % on an as-received basis.

IV.J. Anti-Foam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent, preferably 0.001 to 0.5 wt %, more preferably 0.001 to 0.2 wt %, still more preferably 0.0001 to 0.15 wt % (on an as-received basis) based on the total weight of the lubricating oil composition.

IV.K. Corrosion Inhibitors and Antirust Additives

Antirust additives (or corrosion inhibitors) are additives that protect lubricated metal surfaces against chemical attack by water or other contaminants. One type of antirust additive is a polar compound that wets the metal surface preferentially, protecting it with a film of oil. Another type of antirust additive absorbs water by incorporating it in a water-in-oil emulsion so that only the oil touches the surface. Yet another type of antirust additive chemically adheres to the metal to produce a non-reactive surface. Examples of suitable additives include zinc dithiophosphates, metal phenolates, basic metal sulfonates, fatty acids and amines. Such additives may be used in an amount of 0.01 to 5 wt %, preferably 0.01 to 1.5 wt % on an as-received basis.

In addition to the ZDDP anti-wear additives which are essential components of the present disclosure, other anti-wear additives can be present, including zinc dithiocarbamates, molybdenum dialkyldithiophosphates, molybdenum dithiocarbamates, other organo molybdenum-nitrogen complexes, sulfurized olefins, etc.

The term "organo molybdenum-nitrogen complexes" embraces the organo molybdenum-nitrogen complexes described in U.S. Pat. No. 4,889,647. The complexes are reaction products of a fatty oil, diethanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 $cm^{-1}$ and an amide carbonyl band at 1620 $cm^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used in the present disclosure are tri-nuclear molybdenum-sulfur compounds described in EP 1,040,115 and WO 99/31113 and the molybdenum complexes described in U.S. Pat. No. 4,978,464.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

General Methods

The lube properties of the products produced in Examples 1 and 2 were evaluated as provided. The kinematic viscosity (KV) of the products was measured using ASTM standard D-445 and reported at temperatures of 100° C. (KV100) or 40° C. (KV40). The viscosity index (VI) was measured according to ASTM standard D-2270 using the measured kinematic viscosities for each product. The Noack volatility of the products was measured according to ASTM standard D-5800. The pour point of the products was measured according to ASTM standard D-5950. The rotating pressure vessel oxidation test (RPVOT) break time was measured according to ASTM standard ASTM D-2272.

In the present and following examples, unless otherwise stated, the $C_{20}$ uPAO dimer used was an approximate mixture of vinylidenes and trisubstituted olefins at a weight ratio of vinylidenes to trisubstituted olefins in the range from 20/80 to 60/40. The C20 uPAO dimer was prepared according to the method described in Example 1 of U.S. Patent Publication No. 2013/0090277 A1, the entirety of which is incorporated herein by reference. Thus, the C20 uPAO dimers would take the following predominant forms:

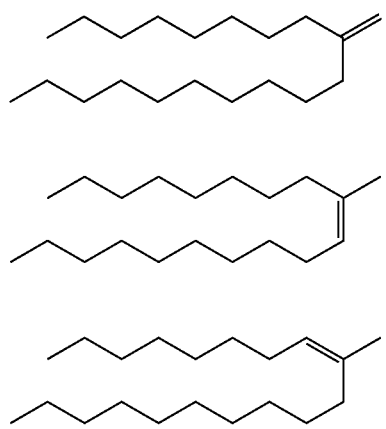

Example 1—Acid Catalyzed Synthesis of Product I Containing Compound-I Corresponding in Structure to Formula (F-I)

Anisole was alkylated with a $C_{20}$ uPAO dimer by acid catalyst as shown below in Scheme 1 to form Product I containing Compound-I.

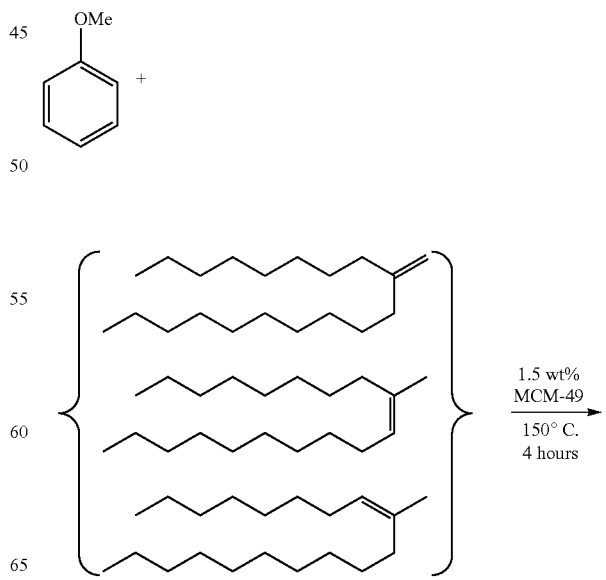

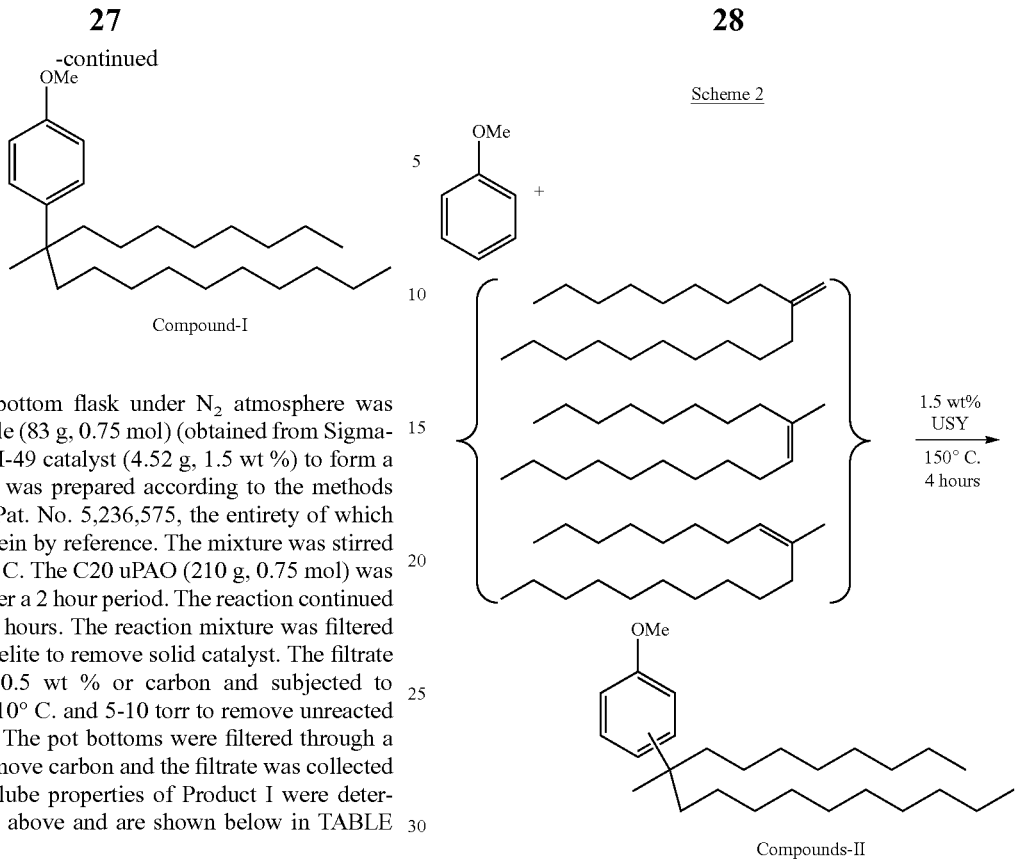

Compound-I

A glass round bottom flask under $N_2$ atmosphere was charged with anisole (83 g, 0.75 mol) (obtained from Sigma-Aldrich) and MCM-49 catalyst (4.52 g, 1.5 wt %) to form a mixture. MCM-49 was prepared according to the methods described in U.S. Pat. No. 5,236,575, the entirety of which is incorporated herein by reference. The mixture was stirred and heated to 150° C. The C20 uPAO (210 g, 0.75 mol) was added dropwise over a 2 hour period. The reaction continued for an additional 2 hours. The reaction mixture was filtered through a bed of Celite to remove solid catalyst. The filtrate was treated with 0.5 wt % or carbon and subjected to distillation up to 210° C. and 5-10 torr to remove unreacted anisole and olefin. The pot bottoms were filtered through a bed of Celite to remove carbon and the filtrate was collected as Product I. The lube properties of Product I were determined as provided above and are shown below in TABLE IV.

TABLE IV

| Lube Properties | |
|---|---|
| KV100 (cSt) | 4.68 |
| KV40 (cSt) | 27.9 |
| VI | 74 |
| Noack volatility (%) | 13.3 |
| Pour Point (° C.) | −60 |
| RPVOT (minutes) | 327 |

Figure 2:
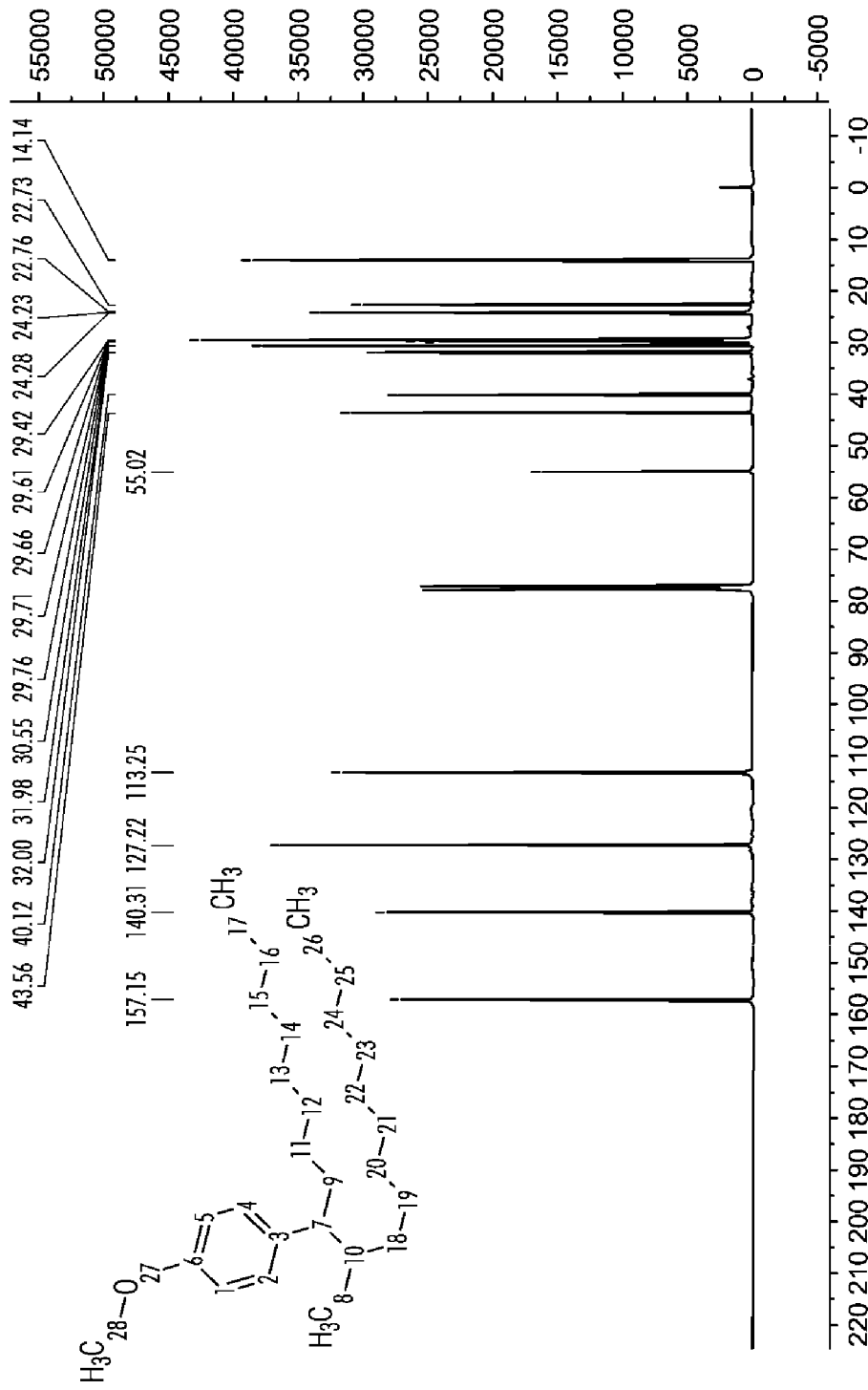
FIG. 2 illustrates $^{13}$C NMR spectra of Product I.

The $^1$H NMR and $^{13}$C NMR spectra of Product I were determined and are shown in FIGS. 1 and 2, respectively. Both $^{13}$C NMR and $^1$H NMR data indicate that Product I contains nearly exclusively a monoalkylated product. The monoalkylated product nearly exclusively exists as single isomer (Compound-I), where the benzene ring bonds to a tertiary carbon atom on the alkyl group.

Figure 3:
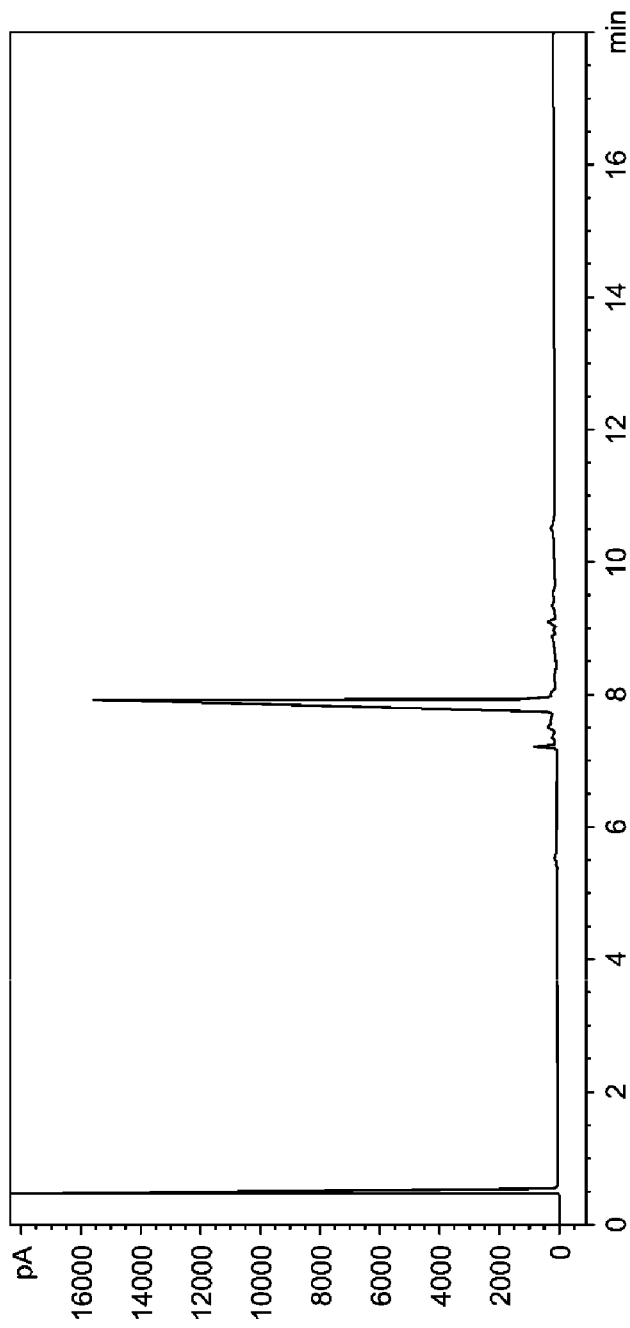
FIG. 3 illustrates gas chromatography (GC) spectra of Product I.

Further, a gas chromatography (GC) analysis was performed on Product I, and a GC spectra for Product I was determined as shown in FIG. 3. The GC spectra for Product I shows a predominantly single peak at 7.9 minutes representing a single product isomer. Smaller peaks between 8 and 10 minutes represent unhydrogenated dimerized C20 dimer. The small peak at 10.5 minutes represents dialkylated anisole.

Example 2: Acid Catalyzed Synthesis of Product II Containing Compounds-II Corresponding in Structure to Formula (F-I)

The same preparation as Example 1 was followed except for the use of USY catalyst instead of MCM-49 to form Product II containing Compounds-II as shown below in Scheme 2.

Scheme 2

Compounds-II

The lube properties of Product II were determined as provided above and is shown below in TABLE V.

TABLE V

| Lube Properties | |
|---|---|
| KV100 (cSt) | 4.42 |
| KV40 (cSt) | 25.2 |
| VI | 73 |
| Noack volatility (%) | 15.1 |
| Pour Point (° C.) | −63 |
| RPVOT (minutes) | 332 |

Figure 4:
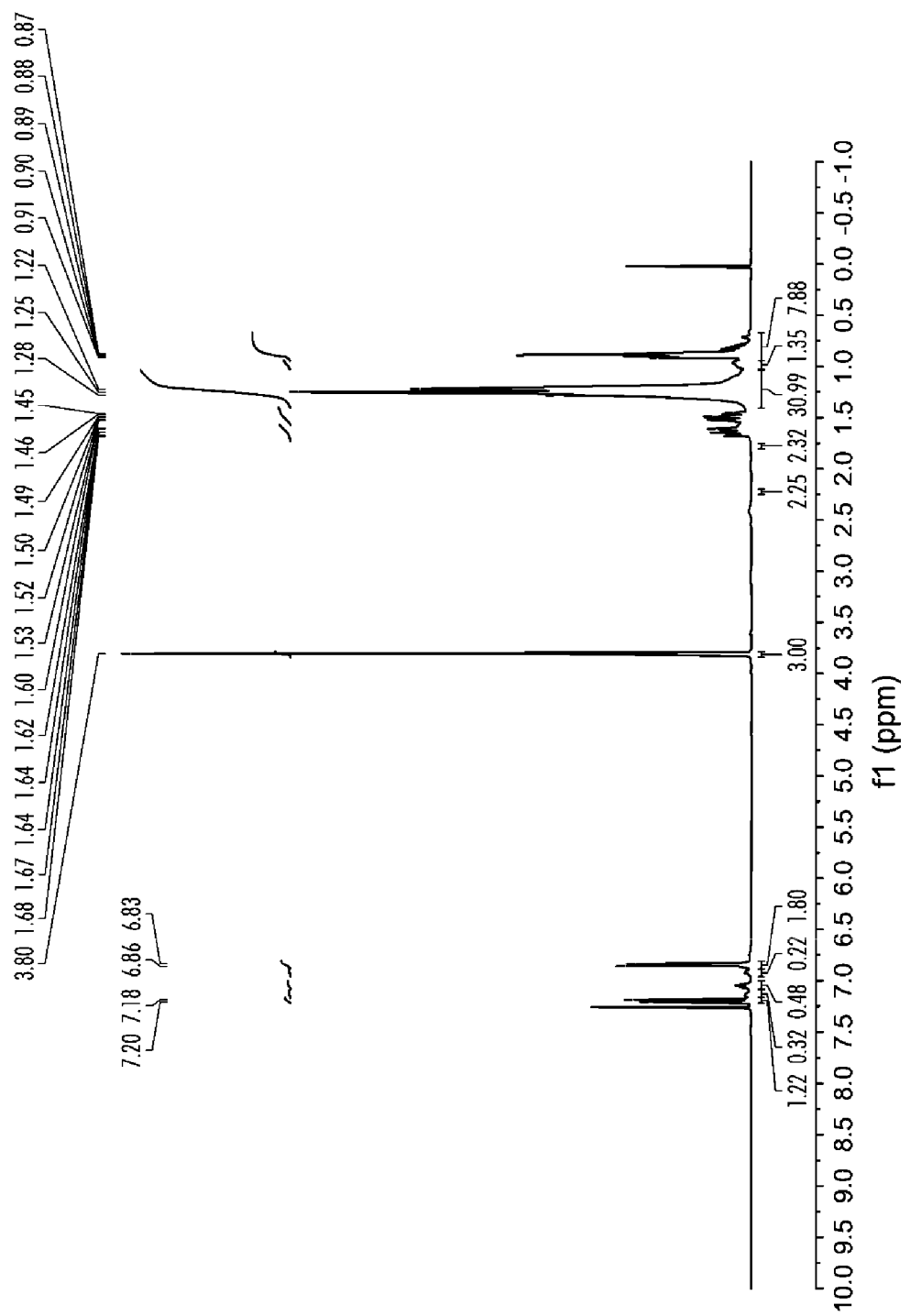
FIG. 4 illustrates $^1$H NMR spectra of Product II in the Examples of this disclosure.
Figure 5:
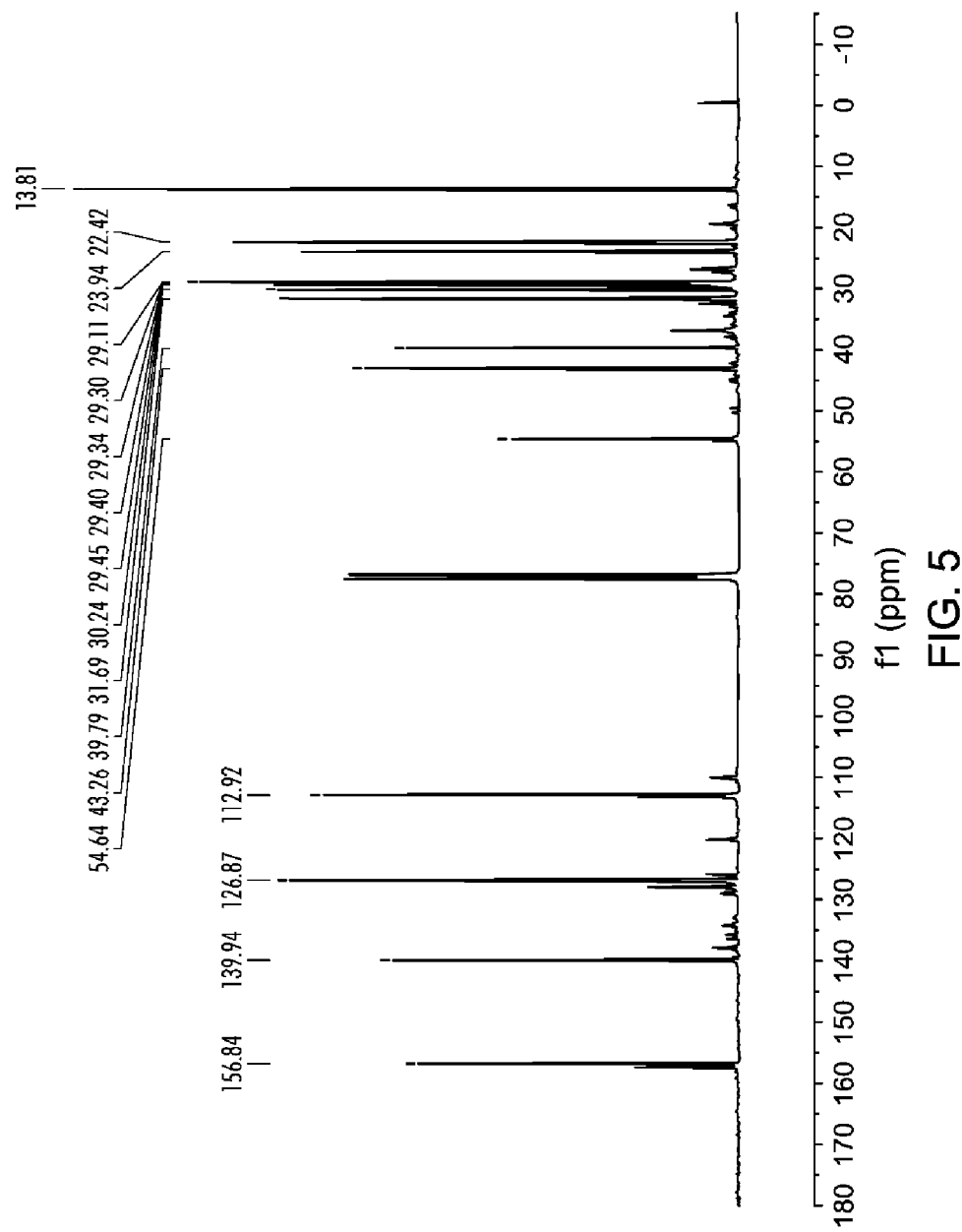
FIG. 5 illustrates $^{13}$C NMR spectra of Product II.

The $^1$H NMR and $^{13}$C NMR spectra of Product II were determined and are shown in FIGS. 4 and 5, respectively.

Figure 6:
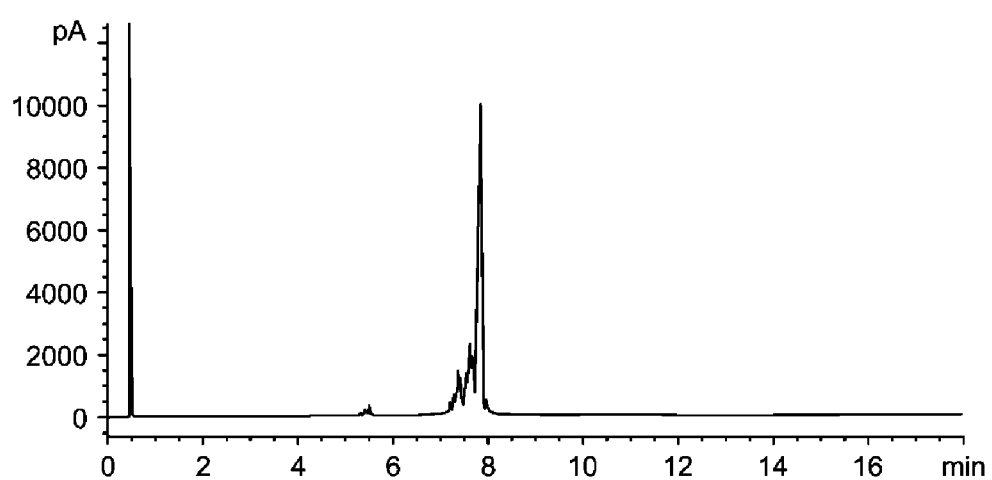
FIG. 6 illustrates GC spectra of Product II.

GC analysis was performed on Product II, and a GC spectra for Product II was determined as shown in FIG. 6. The GC spectra for Product II shows a predominantly monoalkylated product (at 7-8 minute). The monalkylated product exists as a multitude of isomers. The predominant GC peak and molecule isomer at 7.9 minutes is the same as the peak and molecule isomer for Product I. The small peak at 5.5 minutes is trace unreacted C20 PAO olefin.

Example 3—Comparison of Base Stock Properties

Various properties of Product I were compared to commercially available base stocks, Synesstic™ 5 and Esterex™ NP343 (both available from ExxonMobil Chemical Company, 27111 Springwoods Village Parkway, Spring, Tex. 77389, U.S.A.) as shown in TABLE VI below.

TABLE VI

| Property | UNIT | Test Method | Synesstic™ 5 | Product I | Esterex™ NP343 |
|---|---|---|---|---|---|
| Appearance | None | Visual | Bright & Clear | Bright & Clear | Bright & Clear |
| Refractive Index @ 25° C. | None | ASTM D1218 | 1.5220 | 1.486046 | 1.4521 |
| Bromine Number | g(Br)/100 g | ASTM D1159 (mod) | 0.33 | 1.08 | 0 |
| Color, Pt—Co | None | ASTM D1500 | 225 | 0.5 | <1.0 |
| Specific Gravity @ 15.6° C. | None | ASTM D4052 | 0.910 | 0.893 | 0.948 |
| Total Acid Number | mg KOH/g | ASTM D974 (mod) | 0.01 | 0.004 | 0.02 |
| Water | ppm | ASTM D6304 | 11 | 124 | 23.45 |
| Cold Crank Simulator (CCS) Viscosity @-30° C. | cP | ASTM D5293 | 5,243 | 3,900 | 1,183 |
| CCS Viscosity @-35° C. | cP | ASTM D5293 | 10,668 | 7,459 | 2,096 |
| Mini Rotary Viscometer (MRV) Viscosity @-35° C. | cP | ASTM D4684 | 13,568 | 8,717 | 2,286 |
| MRV Viscosity @-40° C | cP | ASTM D4684 | — | 19,358 | 4,289 |
| Brookfield Viscosity @ -40° C. | cP | ASTM D2983 | 70,802 | 19,996 | — |
| Brookfield Viscosity @ -26° C. | cP | ASTM D2983 | 3,950 | 2,586 | 900 |
| Pour Point | ° C. | ASTM D5950 | -39 | -60 | -51 |
| Noack Volatility | wt % | ASTM D5800 | 10.5 | 13.28 | 2.7 |
| Kinematic Viscosity @ 100° C. | cSt | ASTM D445 | 4.77 | 4.681 | 4.31 |
| Kinematic Viscosity @ 40° C. | cSt | ASTM D445 | 28.4 | 27.86 | 19.2 |
| Kinematic Viscosity @ -40° C. | cSt | ASTM D445 | 43600 | 15411(ASTM D7042 Anton Parr) | 3894 |
| Viscosity Index | None | ASTM D2270 | 79 | 74 | 136 |
| RPVOT Neat | minutes | ASTM D2272 | 285 | 327 | 78.5 |
| Density Correction Factor | (g/cm$^3$)/° C. | ASTM D1250 | 0.000527 | 0.000660 | 0.000702 |
| Solubility parameter, calculated (d(i) @ 25° C.) | (cal/cc)$^{1/2}$ | via Fedors Correlation | 8.9 | 8.67 | 9.1 |
| Dielectric Strength | kv | ASTM D877 | 49.0 | 22.5 | 58.1 |
| Kauri-Butanol Value | None | ASTM D1133 | 31.0 | 28.5 | 62.5 |
| 4-Ball Wear (scar diameter) | mm | ASTM D4172 | 0.68 | 0.61 | 0.65 |
| Aniline Point | ° C. | ASTM D611 | 27.9 | 26.4 | 23.5 |
| Evaporation Loss @ 205° C. for 6.5 hour | wt % | ASTM D972 | 15.6 | 75.9 | 5.0 |
| Hydrolytic Stability, total acid number (TAN) Change | mg KOH/g | ASTM D2619 | 0.02 | 0.02 | 0.20 |
| Fire Point, Cleveland Open-Cup (COC) | ° C. | ASTM D92 | 256 | 257 | 291 |
| Flash Point, Pensky-Martens Closed Cup (PMCC) | ° C. | ASTM D93 | 192 | 227 | 245 |
| Flash Point, COC | ° C. | ASTM D92 | 222 | 231 | 265 |

As shown in TABLE VI, Product I has better oxidative stability (RPVOT) than Synesstic™ 5 and Esterex™ NP343. Product I has similar viscosity (KV100) as Synesstic™ 5, but improved low temperature properties (pour point, CCS, MRV, Brookfield, KV @ -40° C.). Product I also has a lower aniline point than Synesstic™ 5, indicating higher polarity and a general improvement in solubilizing strength with regard to additives and deposits. Further, Product I has better hydrolytic stability than Esterex™ NP343. Also, the high polarity of esters (e.g., Esterex™ NP343) often causes incompatibility with seals in automotive engines or industrial equipment.

Example 4—Stribeck and Traction Analysis for Product I, Synesstic™ 5 and Esterex™ NP343

Figure 7A:
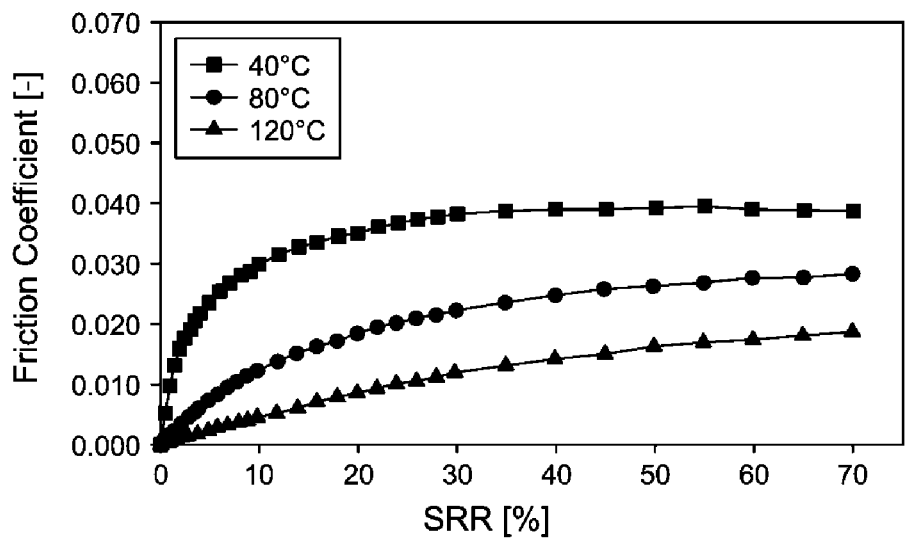
FIGS. 7a and 7b illustrate a traction curve and a Stribeck curve, respectively, for Product I.
Figure 7B:
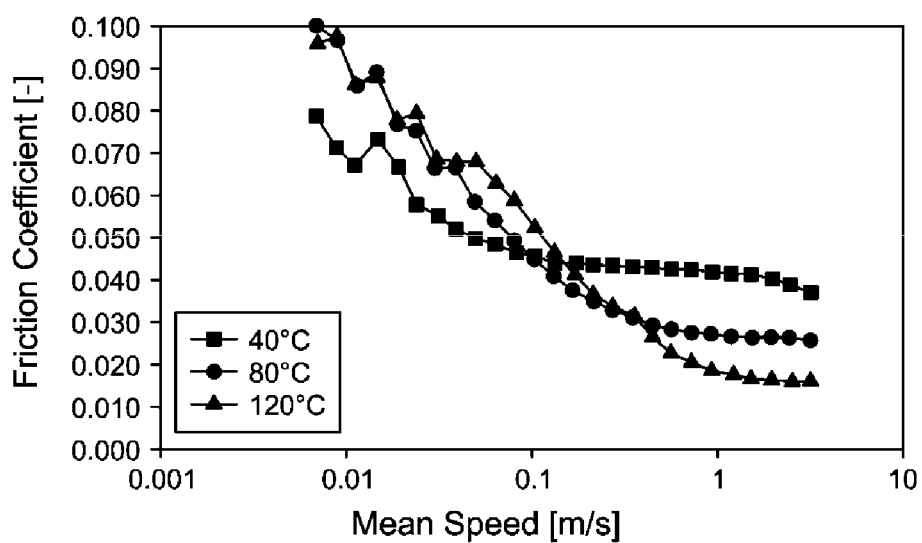
Figure 8A:
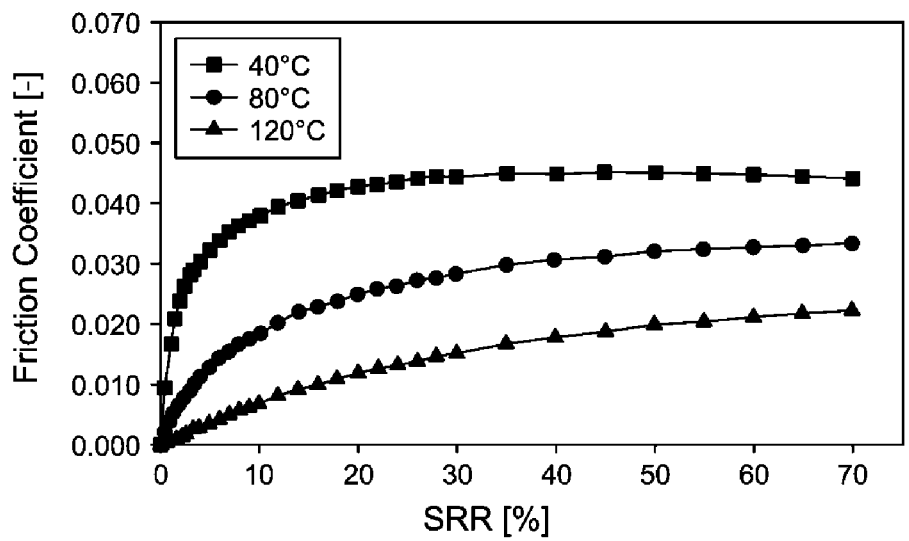
FIGS. 8a and 8b illustrate a traction curve and a Stribeck curve, respectively, for Synesstic™ 5.
Figure 8B:
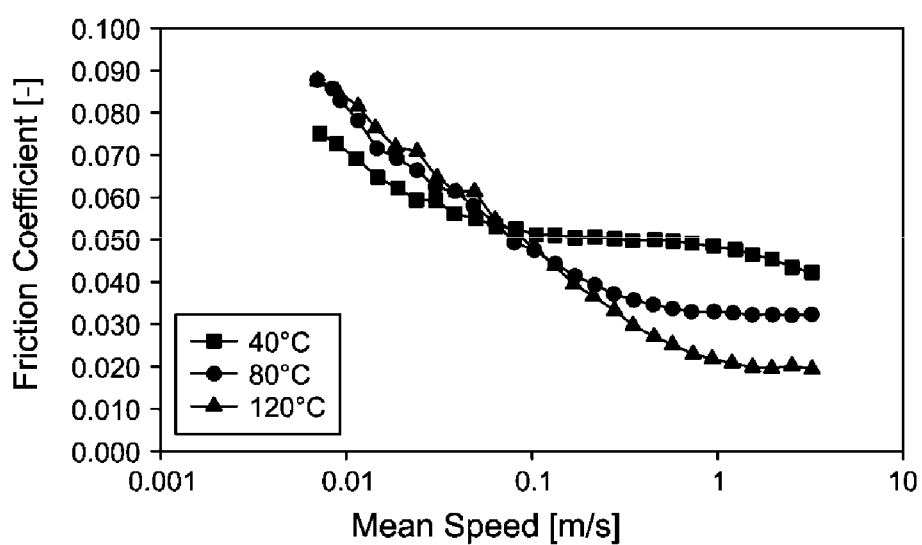
Figure 9A:
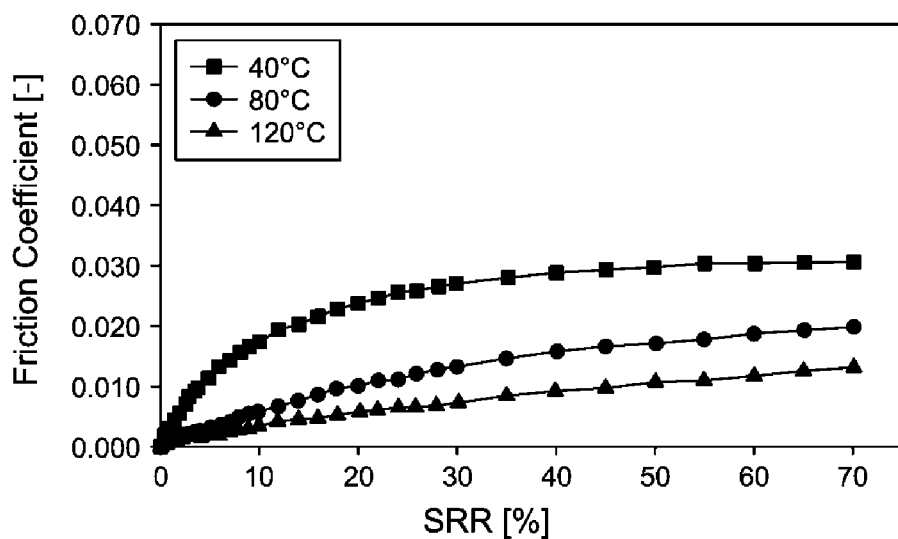
FIGS. 9a and 9b illustrate a traction curve and a Stribeck curve, respectively, for Esterex™ NP343.
Figure 9B:
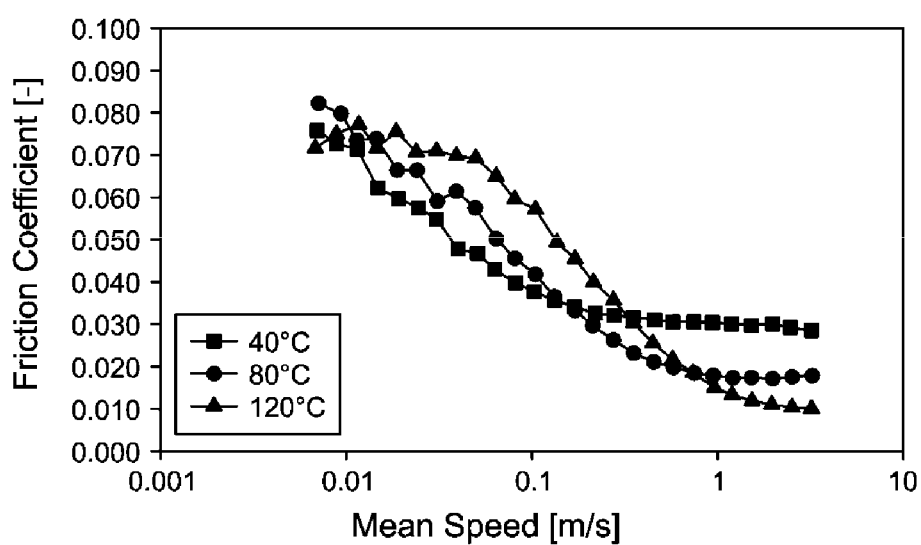

Traction curves for Product I, Synesstic™ 5, and Esterex™ NP343 were developed using a rolling ball on disk method. Each base stock was examined under slide to roll ratios (SRR) of 0-70% with a mean speed of 2.0 m/s and at three different temperatures (40, 80, 120° C.). The Stribeck curve was developed with a SRR of 50%, a mean speed of 0.007 to 3.0 m/s and at three different temperatures (40° C., 80° C., 120° C.). The traction curves for Product I, Synesstic™ 5, and Esterex™ NP343 are shown in FIGS. 7a, 8a, and 9a, respectively, the Stribeck curves for Product I, Synesstic™ 5, and Esterex™ NP343 are shown in FIGS. 7b, 8b, and 9b, respectively. These data show Product I has a lower coefficient of friction than Synesstic™ 5, which represents improved energy efficiency.

Example 5—Oil Formulations Comparisons

Example 5a: Industrial Oil Formulations

Three industrial oil formulations of viscosity weight ISO VG 320 (Formulations 1-3) were prepared as shown in TABLE VII below. The formulations contained the same Group IV primary base stocks (obtained from ExxonMobil Chemical Company) and additives (obtained from Elco Corporation having an address at 1000 Belt Line Avenue, Cleveland, Ohio 44109-2848 U.S.A.). Each formulation also included 10 wt % of different Group V components, namely Synesstic™ 5, Product I and Esterex™ NP343.

TABLE VII

| | | Formulation No. | | |
|---|---|---|---|---|
| | | 1 | 2 | 3 |
| Components (wt %) | SpectraSyn ™ 6 (31 cSt) | 25.42 | 25.60 | 23.92 |
| | SpectraSyn Elite ™ 150 (1645 cSt) | 63.08 | 62.90 | 64.58 |
| | Synesstic ™ 5 (28.4 cSt) | 10.0 | | |
| | Product I (27.86 cSt) | | 10.0 | |
| | Esterex ™ NP343 (19.2) | | | 10.0 |
| | Elco 393D (42) | 1.5 | 1.5 | 1.5 |
| | Total | 100.0 | 100.0 | 100.0 |
| Properties | Measurement Protocol | 1 | 2 | 3 |
| KV40, cSt | ASTM D445 | 318.8 | 318.9 | 320.1 |
| KV100, cSt | ASTM D445 | 40.69 | 40.57 | 41.84 |
| Viscosity Index (VI) | ASTM D2270 | 182 | 181 | 186 |
| Pour Point, ° C. | ASTM D5950 | −54 | −54 | −54 |
| Brookfield @ −26° C., cP | ASTM D2983 | 33,960 | 33,120 | 32,640 |
| Brookfield @ −40° C., cP | ASTM D2983 | 295,000 | 238,000 | 240,000 |
| Foam Seq I | ASTM D892 | 650/285 | 550/130 | 550/10 |
| Foam Seq II | | 60/0 | 20/0 | 5/0 |
| Foam Seq III | | 560/100 | 450/10 | 70/0 |
| RPVOT, minutes | ASTM D2272 | 368 | 409 | 371 |
| 4-Ball Wear, mm | ASTM D4172 | 0.50 | 0.48 | 0.49 |
| Taper Rolling Bearing (CEC -L45-A-99) | Relative Viscosity Loss, % at 20 hours | 0.5 | 0.5 | 0.2 |
| | Relative Viscosity Loss, % at 100 hours | −1.6 | −1.7 | 0.0 |

Base stocks containing aromatic groups are known to contribute to poor foaming performance. However, Formulation 2 containing Product I had better foam performance compared to the formulation containing Synesstic™ 5. Further, Formulation 2 containing Product I displayed superior oxidative stability (RPVOT).

Example 5b: Automotive Gear Oil Formulations

Three different automotive gear oil formulations of viscosity grade 80W90 (Formulations 4-6) were prepared as shown in TABLE VIII below. The primary base stocks (Group II/IV) (obtained from ExxonMobil Chemical Company) and additives (HiTEC® 385, obtained from Afton Chemical Corporation having an address at 500 Spring Street, Richmond, Va. 23219, U.S.A.) were incorporated. Each of the three formulations utilized a different Group V material at a 10 wt % treat rate.

TABLE VIII

| | | Formulation No. | | |
|---|---|---|---|---|
| | | 4 | 5 | 6 |
| Components (wt %) | EHC 50 GRP II (5.4 cSt) | 50.8 | 50.6 | 50.1 |
| | SpectraSyn Elite 150 (157 cSt) | 31.7 | 31.9 | 32.4 |
| | Synesstic ™ 5 (4.773 cSt) | 10.0 | | |
| | Product I (4.681 cSt) | | 10.0 | |
| | Esterex ™ NP343 (4.4 cSt) | | | 10.0 |
| | HiTEC ® 385 (15.93 cSt) | 7.5 | 7.5 | 7.5 |
| | Total | 100.0 | 100.0 | 100.0 |
| KV40, cSt | ASTM D445 | 99.98 | 100.5 | 95.17 |
| KV100, cSt | ASTM D445 | 14.75 | 14.89 | 14.67 |
| VI | ASTM D2270 | 154 | 155 | 161 |
| Pour Point, ° C | ASTM D5950 | −24 | −27 | −24 |
| Brookfield @−26° C., cP | ASTM D2983 | 19,560 | 20,160 | 19,650 |
| Brookfield @−40° C., cP | ASTM D2983 | 1,620,000 | 741,000 | 360,000 |
| Appearance | visual | B&C | B&C | B&C |
| Foam Seq I | ASTM D892 | 550/20 | 550/20 | 550/5 |
| Foam Seq II | | 55/0 | 80/0 | 80/0 |
| Foam Seq III | | 390/5 | 350/10 | 530/70 |
| RPVOT, minutes | ASTM D2272 | 95 | 112 | 124 |
| 4-Ball Wear, mm | ASTM D4172 | 0.74 | 0.80 | 0.57 |
| Taper Rolling Bearing (CEC -L45-A-99) | Relative Viscosity Loss, % at 20 hours | 0.6 | 0.1 | 0.0 |
| | Relative Viscosity Loss, % at 100 hours | 0.5 | 0.7 | 0.4 |

Formulation 5 containing Product I demonstrated better low temperature performance (Brookfield @−40° C.) than Formulation 4 containing Synesstic™ 5.

Example 5c: Engine Oil Formulations

Engine oil formulations of viscosity grade 5W30 and 10W30 containing 10 wt % of Product I as a co-base stock (Formulation Nos. 7-9) were prepared as shown in TABLE IX below. The formulations use either a Group III (Yubase® 4 commercially available form SK Lubricants Co., Ltd. having an address at 26, Jongro, Jongro-Gu, Seoul 110-728, Korea) or Group IV (SpectraSyn™ 4) base stock as the primary base stock. The base stock SpectraSyn Elite™ 150 is also a Group IV base stock available commercially from ExxonMobil Chemical Company. The additive Infineum P6003™ is commercially available from Infineum USA L.P., Linden Business and Technology Centre, 1900 East Linden Avenue, P.O. Box 735. Linden, N.J. 07036, U.S.A.

The present disclosure has been described above with reference to numerous embodiments and specific examples. Many variations will suggest themselves to those skilled in this art in light of the above detailed description. All such obvious variations are within the full intended scope of the appended claims.

TABLE IX

| Formulation No. | | 7 | 8 | 9 | 10 | 11 | 12 | 13 | 14 |
|---|---|---|---|---|---|---|---|---|---|
| Components (wt %) | Yubase ® 4 (4.237 cSt) | — | | | | 70.70 | 60.70 | 60.70 | 60.70 |
| | SpectraSyn ™ 4 (4.144 cSt) | 70.00 | 60.00 | 60.00 | 60.00 | — | | | |
| | Synesstic ™ 5 (4.773 cSt) | | 10.00 | | | | 10.00 | | |
| | Product I (4.681 cSt) | | | 10.00 | | | | 10.00 | |
| | Esterex ™ NP343 (4.4 cSt) | | | | 10.00 | | | | 10.00 |
| | SpectraSyn Elite ™ 150 (157 cSt) | 18.00 | 18.00 | 18.00 | 18.00 | 17.30 | 17.30 | 17.30 | 17.30 |
| | Infineum P6003 ™ (146.1 cSt) | 12.00 | 12.00 | 12.00 | 12.00 | 12.00 | 12.00 | 12.00 | 12.00 |
| | Total | 100.00 | 100.00 | 100.00 | 100.00 | 100.00 | 100.00 | 100.00 | 100.00 |
| Viscosity Grade | | 5W30 | 5W30 | 5W30 | 5W30 | 10W30 | 10W30 | 10W30 | 5W30 |
| KV40, cSt | | 60.78 | 61.49 | 61.71 | 58.32 | 60.31 | 61.89 | 61.92 | 58.44 |
| KV100, cSt | | 10.56 | 10.62 | 10.62 | 10.39 | 10.39 | 10.55 | 10.54 | 10.31 |
| VI | | 165 | 164 | 163 | 169 | 162 | 161 | 161 | 166 |
| Pour Point, ° C. | | −60 | −66 | −66 | −66 | −24 | −30 | −27 | −27 |
| CCS @ −25° C., cP | | — | — | — | — | 3769 | 3,835 | 3,806 | — |
| CCS @ −30° C., cP | | 4834 | 4,886 | 4,906 | 4,333 | 6769 | — | — | 5,902 |
| MRV @ −30° C., cP | | 5014 | — | — | — | 22294 | 13,369 | 15,057 | — |
| MRV @ −35° C., cP | | 8723 | 10,782 | 10,629 | 9,362 | 36075 | — | — | 44,390 |
| HTHS @ 150° C., cP | | 3.365 | 3.395 | 3.394 | 3.388 | 3.373 | 3.419 | 3.389 | 3.460 |
| NOACK @ 250° C., % weight loss | | 9.8 | 9.2 | 10.2 | 9.1 | 11.6 | 11.4 | 12.8 | 10.7 |

As shown in TABLE IX, Product I has similar viscometric performance in engine oil lubricants as Synesstic™ 5.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

What is claimed is:

1. A process for making a compound of the following formula (F-I):

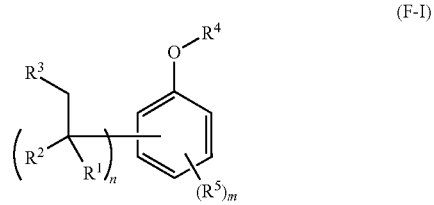

(F-I)

wherein:

$R^1$ is a $C_6$-$C_{5000}$ alkyl group;

$R^2$ is a $C_4$-$C_{5000}$ alkyl group;

$R^3$ at each occurrence is independently hydrogen or a $C_1$-$C_{500}$ alkyl group;

$R^4$ is a $C_1$-$C_{50}$ alkyl group or an unsubstituted or substituted phenyl group;
$R^5$ is hydrogen or a $C_1$-$C_{30}$ alkyl group;
n is 1, 2, 3, or 4; and
m+n is 5;
comprising:
reacting a compound having the following formula (F-Ia):

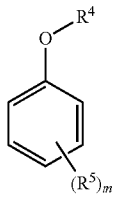

(F-Ia)

with an olefin-containing material comprising a compound having the following formula (F-Ib):

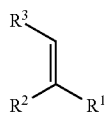

(F-Ib)

in the presence of an acid catalyst.

2. The process of claim 1, wherein the olefin-containing material comprises at least about 75 wt% of the compound of formula (F-Ib) where $R^3$ is hydrogen.

3. The process of claim 1, wherein the olefin-containing material comprises at least about 50 wt% of the compound of formula (F-Ib) where $R^3$ is a $C_1$-$C_{100}$ alkyl group.

4. The process of claim 1, wherein the olefin-containing material comprises a mixture of: (i) about 1.0 to about 99 wt% of the compound of formula (F-Ib) where $R^3$ is hydrogen; and (ii) about 1.0 to about 99 wt% of the compound of formula (F-Ib) where $R^3$ is a $C_1$-$C_{100}$ alkyl group.

5. The process of claim 1, wherein the olefin-containing material has an isotacticity of at least about 60 mol%.

6. The process of claim 1, wherein the acid catalyst is a solid acid catalyst selected from the group consisting of a solid Lewis acid, an acid clay, a polymeric acidic resin, silica-alumina, a mineral acid and a combination thereof.

7. The process of claim 1, wherein the acid catalyst comprises one or more molecular sieve having a framework structure selected from the group consisting of BEA, EUO, FAU, FER, HEU, MEL, MFI, MOR, MRE, MTW, MTT, MWW, OFF, and combinations thereof.

8. The process of claim 7, wherein the molecular sieve is selected from the group consisting of ZSM-5, ZSM-11, ZSM-12, ZSM-23, ZSM-35, ZSM-48, ZSM-50, Zeolite Beta, MCM-56, MCM-22, MCM-36, MCM-49, zeolite Y, zeolite X, and combinations thereof.

9. The process of claim 1, wherein at least about 50 mol% of the compounds produced have the moiety comprising $R^1$, $R^2$, and $R^3$ bonded to the phenyl ring at a position para to the —O—$R^4$ moiety.

10. A lubricant base stock comprising one or more of the compound of the following formula (F-I):

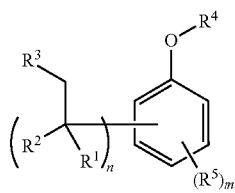

(F-I)

wherein:
$R^1$ is a $C_6$-$C_{5000}$ alkyl group;
$R^2$ is a $C_4$-$C_{5000}$ alkyl group;
$R^3$ at each occurrence is independently hydrogen or a $C_1$-$C_{500}$ alkyl group;
$R^4$ is a $C_1$-$C_{50}$ alkyl group or an unsubstituted or substituted phenyl group;
$R^5$ is hydrogen or a $C_1$-$C_{30}$ alkyl group;
n is 1, 2, 3, or 4; and
m+n is 5;
wherein the lubricant base stock has one or more of:
(i) a hydrolytic stability, measured according to ASTM D-2619, of about 0.01 to about 1.0 mg KOH/g;
(ii) a solubility of measured according to Fedors Correlation, of about 8 to about 10 d(i) at 25° C. (cal/cc)^1/2; and
(iii) a rotating pressure vessel oxidation test (RPVOT) break time, measured according to ASTM D-2272, of at least about 200 minutes.

11. A formulated lubricant composition comprising one or more of the lubricant base stocks of claim 10 in an amount from about 5 wt% to about 90 wt%, based on the total weight of the formulated lubricant composition.

* * * * *